(12) United States Patent
Farnum

(10) Patent No.: US 9,851,346 B2
(45) Date of Patent: Dec. 26, 2017

(54) CHEMICAL SENSITIVITY SCREENING TEST

(71) Applicant: BRYSON PATENTS INC., King City (CA)

(72) Inventor: Bryan Christopher Farnum, King City (CA)

(73) Assignee: Bryson Patents Inc., King (CA)

( * ) Notice: Subject to any disclaimer, the term of this patent is extended or adjusted under 35 U.S.C. 154(b) by 128 days.

(21) Appl. No.: 14/966,232

(22) Filed: Dec. 11, 2015

(65) Prior Publication Data

US 2016/0169872 A1    Jun. 16, 2016

Related U.S. Application Data

(60) Provisional application No. 62/090,441, filed on Dec. 11, 2014.

(51) Int. Cl.
| | |
|---|---|
| *G01N 33/52* | (2006.01) |
| *G01N 33/58* | (2006.01) |
| *G01N 21/75* | (2006.01) |
| *G01N 21/77* | (2006.01) |
| *G01N 21/78* | (2006.01) |
| *C12Q 1/68* | (2006.01) |
| *C12M 1/00* | (2006.01) |

(52) U.S. Cl.
CPC .......... *G01N 33/521* (2013.01); *G01N 21/75* (2013.01); *G01N 21/77* (2013.01); *G01N 33/52* (2013.01); *C12Q 1/6816* (2013.01); *G01N 21/78* (2013.01); *G01N 33/582* (2013.01); *G01N 33/585* (2013.01)

(58) Field of Classification Search
CPC ..... C12Q 1/6816; C12M 21/18; G01N 21/77; G01N 21/78; G01N 33/582; G01N 33/585; G01N 33/52; G01N 33/521
See application file for complete search history.

(56) References Cited

U.S. PATENT DOCUMENTS

2014/0154808 A1 *  6/2014  Patel ................ G01K 3/04
                                                    436/1

\* cited by examiner

*Primary Examiner* — Jennifer Wecker
(74) *Attorney, Agent, or Firm* — Benoit & Cote Inc.

(57) ABSTRACT

The present document describes a screening composition comprising a marker compound, chosen from at least one of iodine, and fluorescein; eosin Y, erythrosine, ponceau S, calcein, a catalyst, chosen from at least one boron trioxide ($B_2O_3$), potassium (K), Gallium (III) oxide ($Ga_2O_3$), Nickel (II) oxide (NiO), Vanadium (V) oxide ($V_2O_5$), magnesium oxide (MgO), a bismuth oxide chosen from bismuth subcarbonate [$Bi_2O_2(CO_3)$], bismuth chloride oxide (BiClO), and bismuth oxide ($Bi_2O_3$), cesium bromide (CsBr), lanthanum (III) oxide ($La_2O_3$), molybdenum (VI) oxide ($MoO_3$), neodymium oxide ($Nd_2O_3$), Nickel (II) carbonate anhydrous ($NiCO_3$); and a pigment, chosen from at least one of scandium (III) oxide ($Sc_2O_3$), Lead (IV) oxide ($PbO_2$), Sulfur (S) powder, and Tungsten (VI) oxide ($WO_3$), chromium (III) oxide ($Cr_2O_3$), copper (II) oxide (CuO), copper (I) oxide ($Cu_2O$), iron (III) oxide ($Fe_2O_3$), lead (II) oxide (PbO). The document also describes method of using the same.

19 Claims, 7 Drawing Sheets

| Water | | | | |
|---|---|---|---|---|
| ASA | 325 mg | 650 mg | 975 mg | |
| Ibuprofene | 200 mg | 400 mg | 600 mg | |

Fig. 9

| | |
|---|---|
| Water + Alcohol | |
| ASA (650 mg) + Alcohol | |
| Ibuprofene (400 mg) + Alcohol | |
| Acetaminophen (650 mg) + Alcohol | |

Fig. 10

| | 3 mins | 5 mins |
|---|---|---|
| Water |  | N/A |
| Cane Sugar |  | N/A |
| White icing sugar |  | N/A |
| Sucralose |  |  |
| NaCl |  |  |
| Himalayan pink salt (2-3% polyhalite) |  |  |

|  | 3 mins | 5 mins |
|---|---|---|
| Individual 1 |  |  |
| Individual 2 |  |  |

CHEMICAL SENSITIVITY SCREENING TEST

CROSS-REFERENCE TO RELATED APPLICATIONS

This application claims priority of U.S. provisional patent application 62/090,441, filed on Dec. 11, 2015, the specification of which is hereby incorporated by reference.

BACKGROUND (a) Field

The subject matter disclosed generally relates to chemical screening composition for testing the screening a specimen of a substance for causing adverse effects to a subject, and more specifically to test strip comprising the same.

(b) Related Prior Art

The sensitivity, intolerance or allergy to chemical substances such as drugs, cosmetics and foods are difficult to predict for any given individual. Drug intolerance or drug sensitivity is a lower threshold to the normal pharmacologic action of a drug. It is not to be confused with drug allergy. Drug intolerance is uncommon and idiopathic, thus extremely difficult to predict except in persons with a prior history or a family history of intolerance to that specific drug. Some drug intolerances are known to result from genetic variants of drug metabolism.

A drug intolerance, which is often a milder, non-immune-mediated reaction, does not depend on prior exposure. Most people who believe they are allergic to aspirin are actually suffering from a drug intolerance. Drug formulations often contain many different substances, including dyes, which could cause allergic reactions. This can cause an allergic reaction on the first administration of a drug. For example, a person who developed an allergy to a red dye will be allergic to any new drug which contains that red dye.

Testing for allergies may be performed by medical professionals, but normally necessitates a visit to a clinic or hospital in order to physically expose the individual to the chemical substances believed to cause the allergy and verify if an allergic reaction occurs after exposure. Although most of such controlled exposures are benign to the subject, complications may nevertheless arise and cause life threatening complications. Furthermore, such controlled tests will usually not allow for the testing of interactions between two or more chemical substances. Also, similar testing protocols do not exist for all chemical substances and they may not be suitable for testing for intolerances or sensitivities.

Thus, there is a need for quick and simple compositions for determining if a given substance will trigger adverse effects to an individual upon consumption, thus testing the sensitivity of individuals to chemical substances. Also, there is a need for quick and simple methods for testing the overall sensitivity of subjects to chemical substances.

SUMMARY

According to another embodiment, there is provided a screening composition comprising:
  a marker compound, chosen from at least one of iodine, and fluorescein;
  a catalyst, chosen from at least one boron trioxide ($B_2O_3$), potassium (K), Gallium (III) oxide ($Ga_2O_3$), Nickel (II) oxide (NiO), Vanadium (V) oxide ($V_2O_5$) and magnesium oxide (MgO); and
  a pigment, chosen from at least one of scandium (III) oxide ($Sc_2O_3$), Lead (IV) oxide ($PbO_2$), Sulfur (S) powder, and Tungsten (VI) oxide ($WO_3$).

According to another embodiment, there is provided a screening strip comprising
  an solid phase layer, comprising an adsorbent; and
  a screening composition according to the present invention.

The following terms are defined below.

The term "substance" is intended to mean a kind of matter having uniform or relatively uniform properties, and which may be composed of one or more ingredients. For example, the substance may be, without limitations, an example of a drug, food, herb, a supplement, chemical, cosmetic, etc., and mixtures thereof, that may be tested with the screening test of the present invention. According to an embodiment, more than one substance may be combined in the specimen, so that the overall sensitivity/toxicity of the mixture may be tested.

The term "specimen" is intended to mean an example of the substance to be tested with the composition/strip tests of the present invention, which is regarded as typical of its class or group.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

The substance is a sample of the anti-depressant Dextroamphetamine XR 5 mg. The test strip turns a dark color, and does not possess the bright yellow color of the positive test.

Figure 6:
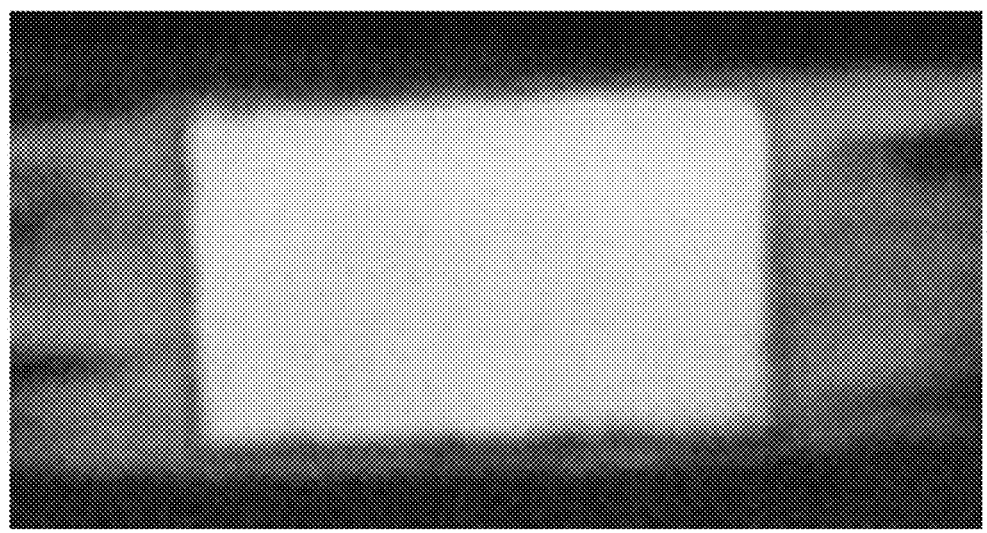

FIG. 6 illustrates a strip test according to the present invention that has been contacted with a sample of a substance that does not cause an adverse effect to an individual. The substance is a sample of the blood pressure medication candesartan 8 mg. The test strip glows a bright yellow color.

Figure 7:
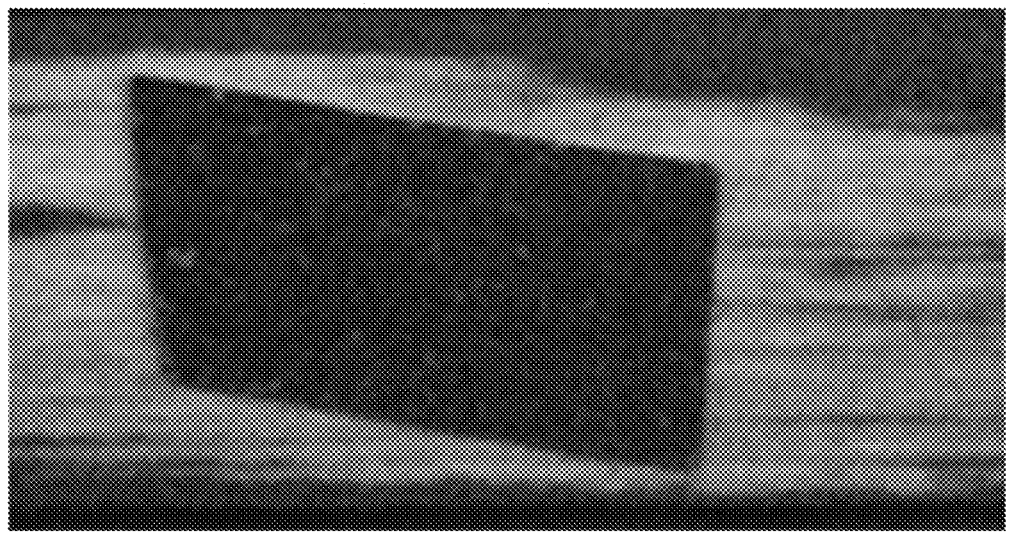

FIG. 7 illustrates a strip test according to the present invention that has been contacted with a sample of a substance that may cause an adverse effect to an individual. The substance is a sample of the anti-depressant Dextroamphetamine XR 5 mg. The test strip turns a dark color, and does not possess the bright yellow color of the positive test.

Figure 8:
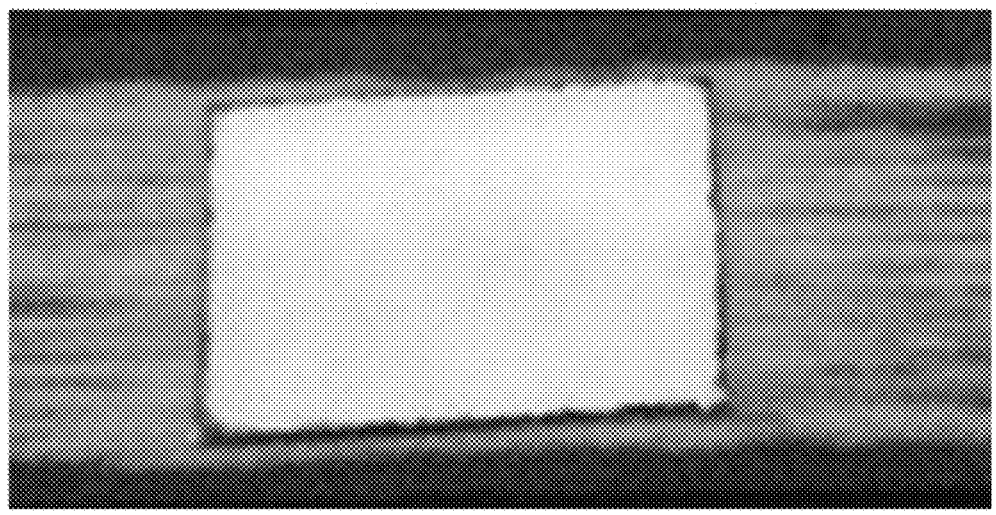

FIG. 8 illustrates a strip test according to the present invention that has been contacted with a sample of a substance that does not cause an adverse effect to an individual. The substance is a sample of the blood pressure medication candesartan 8 mg. The test strip glows a bright yellow color.

FIG. 9 illustrates strip tests according to the present invention that has been contacted with various pain relief medication.

FIG. 10 illustrate strip tests according to the present invention that has been contacted with various pain relief medication dissolved in 50% water and 50% ethanol (40% vol/vol).

Figure 11:
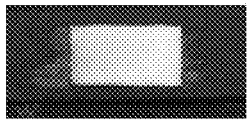
Figure 11:
Figure 11:
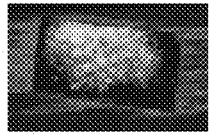
Figure 11:
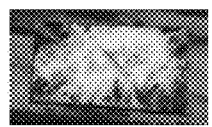
Figure 11:
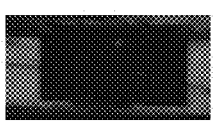
Figure 11:
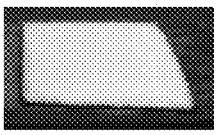
Figure 11:
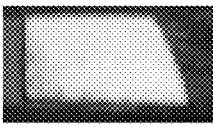
Figure 11:
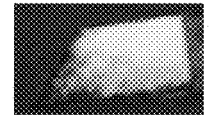
Figure 11:
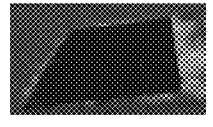

FIG. 11 illustrate strip tests according to the present invention that has been contacted with sweeteners and table salts.

Figure 12:
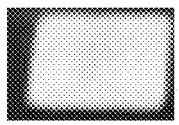
Figure 12:
Figure 12:
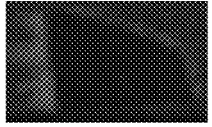
Figure 12:

FIG. 12 illustrate strip tests according to the present invention that has been contacted with urine from two distinct individuals.

DETAILED DESCRIPTION

The present invention concerns a strip test technology to determine if a given substance will trigger adverse effects to an individual upon consumption. The present invention allows the screening of these substances before they are allowed to be ingested on human or animal subjects, in order to provide an a priori indication to the manufacturer as to the potential risks of triggering adverse effects.

According to an embodiment, there is provided a screening composition comprising:
- a marker compound, chosen from at least one of iodine, and fluorescein;
- a catalyst, chosen from at least one boron trioxide ($B_2O_3$), potassium (K), Gallium (III) oxide ($Ga_2O_3$), Nickel (II) oxide (NiO), Vanadium (V) oxide ($V_2O_5$), magnesium oxide (MgO), a bismuth oxide chosen from bismuth subcarbonate [$Bi_2O_2(CO_3)$], bismuth chloride oxide (BiClO), and bismuth oxide ($Bi_2O_3$), cesium bromide (CsBr), lanthanum (III) oxide ($La_2O_3$), molybdenum (VI) oxide ($MoO_3$), neodymium oxide ($Nd_2O_3$), Nickel (II) carbonate anhydrous ($NiCO_3$); and
- a pigment, chosen from at least one of scandium (III) oxide ($Sc_2O_3$), Lead (IV) oxide ($PbO_2$), Sulfur (S) powder, and Tungsten (VI) oxide ($WO_3$), chromium (III) oxide ($Cr_2O_3$), copper (II) oxide (CuO), copper (I) oxide ($Cu_2O$), iron (III) oxide ($Fe_2O_3$), lead (II) oxide (PbO).

According to embodiments, the test formulations for screening of substances are not tied to any specific substances. The formulations of the present invention may be used for the screening of any substances.

According to a second embodiment, there is provided a screening strip comprising:
- an solid phase layer, comprising an adsorbent; and
- a screening composition according to the present invention.

According to an embodiment, the present invention is a highly economical and non-invasive screening test to determine the toxicity of chemicals to individuals in general. The screening test of the present invention tests for sensitivity to chemical substances. According to an embodiment, the test may be used to verify the toxicity of a chemical in a general manner, by contacting a test strip of the present invention with said chemical(s). According to another embodiment, the test may be used to determine the sensitivity of individuals to chemicals that are applied externally on the skin, inhaled; ingested or any other modes of administration to the physical human body (e.g. eye drops, ear drops, asthma inhalers, steroids, any suppositories and intravenous application).

The present invention preferably uses a test strip format and uses marker compounds such as fluorescein. The prepared test strips are contacted with one's bodily fluid, preferably urine, to determine if the individual is sensitive to the tested chemical substance (aka the "specimen of the substance").

Specimen of a substance is defined as any drug, food, herb, supplement, chemical, fragment, particle, molecule and/or any physical mass.

According to an embodiment, screening composition of the present invention may be a test composition activated by contact with the substance to be tested. The specimen of substance can be placed directly into a solvent. In particular embodiments, the solvent may be any suitable solvent, such as water (purified, distilled, etc.), alcohols (such as methanol, ethanol, or the likes), pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, dimethylsulfoxane, nitromethane, propylene carbonate, formic acid, n-Butanol, isopropanol, n-propanol, acetic acid. Preferably, the solvent is distilled water. If the specimen is in tablet form, it should be crushed into a powder form and then added to the solvent. The powder then sits in the solvent until dissolved, for a period ranging from a few second to minutes, hours or even days before it may be tested with the composition and/or strip test of the present invention. Preferably, the contact with the solvent is at least eight hours. A liquid or gel form can be put directly into the solvent. Any capsule contents can be put into the solvent without the encapsulation material. However, the actual capsule material by itself can also be tested. The solvent acts as a preservative. This is why the solvent is important to the test, with respect to the preparation of the specimen. Further, according to some embodiments, the solvent, particularly ethanol, acts as an extraction.

The screening compositions of the present invention comprise a number of components which are detailed below.

Marker Compound

Marker compounds, also known as tracer compounds are chemical compounds which can be used to detect a target, and/or follows the product or course of a reaction. According to an embodiment, the marker compounds used in the present invention are to identify if the substance can cause adverse effects in general. Without wishing to be bound by theory, it is believed that the markers interact with a substance, and cause a chemical reaction that is detected with the composition.

According to an embodiment, a suitable marker in the composition of the present invention includes iodine. The iodine may be free iodine ions (I—), or any other salts of iodine such as NaI, KI, etc. According to an embodiment, the iodine may be provided from a solution such as Gram's iodine solution, which comprises Iodine, 0.33% (w/v), and potassium iodide, 0.66% (w/v) in distilled water. In a preferred embodiment, the Gram's iodine solution is used at about 44% to about 47% w/v of the final solution volume.

According to another embodiment, a suitable marker in the composition of the present invention includes fluorescein. Fluorescein is a synthetic organic compound available as a dark orange/red powder slightly soluble in water and alcohol. It is widely used as a fluorescent tracer for many applications. Fluorescein has an absorption maximum at 494 nm and emission maximum of 521 nm (in water). Fluorescein also has an isosbestic point (equal absorption for all pH values) at 460 nm. Fluorescein is also known as a color additive (D&C Yellow no. 7). The disodium salt form of fluorescein is known as uranine or D&C Yellow no. 8. The color of its aqueous solution varies from green to orange as a function of the way it is observed: by reflection or by transmission, as it can be noticed in bubble levels in which fluorescein is added as a colorant to the alcohol filling the tube to increase the visibility of the air bubble and the precision of the instrument. More concentrated solutions of fluorescein can even appear red. Preferably, the fluorescein is a fluorescein sodium salt. According to an embodiment, the fluorescein may be present at about 0.022% w/v-0.12% w/v, 0.039% w/v-0.12% w/v, or about 0.022% w/v-0.029% w/v or about 0.039% w/v-0.053% w/v, or about 0.039% w/v-0.12% w/v, or about 0.045% w/v-0.061% w/v of the composition, or about 0.053% w/v or about 0.105% w/v.

According to another embodiment, a suitable marker in the composition of the present invention includes Eosin Y. Eosin Y is a form of eosin. It is a red fluorescent dye from the xanthene family. It is most commonly used as a stain for highlighting cytoplasm material in samples. According to an embodiment, the eosin may be present at about 0.0424% w/v-0.057% w/v, or about 0.05% w/v.

According to yet another embodiment, a suitable marker in the composition of the present invention includes Erythrosine Erythrosin or Red No. 3 (also known as erythrosine B, Acid Red 51) is an organoiodine compound, a derivative of fluorone. It is cherry-pink synthetic, primarily used for food coloring, but also used as a biological stain. Erythrosin may be used alone (e.g. as a pure compounds) or as part of the erythrosine yellowish blend which is composed of Eosin Y (10%) and Erythrosin B (90%). Its maximum absorption is 525 nm. According to an embodiment, the erythrosine may be present at about 0.03% w/v-0.045% w/v, or about 0.04% w/v.

According to yet another embodiment, a suitable marker in the composition of the present invention includes ponceau S (stain). Ponceau S, Acid Red 112, or C.I. 27195 is a sodium salt of a diazo dye of a light red color, that may be used to prepare a stain for rapid reversible detection of protein bands on nitrocellulose or polyvinylidene fluoride (PVDF) membranes (Western blotting), as well as on cellulose acetate membranes. A Ponceau S stain is useful because it does not appear to have a deleterious effect on the sequencing of blotted polypeptides and is therefore one method of choice for locating polypeptides on Western blots for blot-sequencing. It is also easily reversed with water washes, facilitating subsequent immunological detection.

According to an embodiment, the ponceau stain may be present at about 0.0005% w/v-0.0015% w/v, or about 0.001% w/v.

Calcein (Disodium Salt) ($C_{30}H_{24}N_2Na_2O_{13}$)—

Calcein is also known as fluorexon sodium salt. It is a fluorescent dye with excitation and emission wavelengths of 494/517 nm, respectively, in pH 9.0. It is used as an indicator for the complexometric determination of calcium and magnesium. It has the appearance of orange crystals. According to an embodiment, the calcein may be present at about 0.004% w/v-0.005% w/v, or about 0.005% w/v.

Catalysts

Catalysis is the increase in the rate of a chemical reaction of one or more reactants due to the participation of an additional substance called a catalyst. Unlike other reagents in the chemical reaction, a catalyst is not consumed by the reaction. With a catalyst, less free energy is required to reach the transition state, but the total free energy from reactants to products does not change. A catalyst may participate in multiple chemical transformations. The effect of a catalyst may vary due to the presence of other substances known as inhibitors or poisons (which reduce the catalytic activity) or promoters (which increase the activity).

Catalyzed reactions have lower activation energy (rate-limiting free energy of activation) than the corresponding uncatalyzed reaction, resulting in a higher reaction rate at the same temperature. However, the mechanistic explanation of catalysis is complex. Catalysts may affect the reaction environment favorably, or bind to the reagents to polarize bonds, e.g. acid catalysts for reactions of carbonyl compounds, or form specific intermediates that are not produced naturally, such as osmate esters in osmium tetroxide-catalyzed dihydroxylation of alkenes, or cause dissociation of reagents to reactive forms, such as chemisorbed hydrogen in catalytic hydrogenation.

According to an embodiment, the composition of the present invention comprises a number of chemical compounds which act as catalysts during the screening process. According to an embodiment, suitable catalyst compounds include but are not limited to boron trioxide ($B_2O_3$), potassium (K), magnesium oxide, gallium (III) oxide ($Ga_2O_3$), Nickel (II) oxide (NiO), and Vanadium (V) oxide ($V_2O_5$), a bismuth oxide chosen from bismuth subcarbonate [$Bi_2O_2(CO_3)$], bismuth chloride oxide (BiClO), and bismuth oxide ($Bi_2O_3$), Boron trioxide ($B_2O_3$)—Also known as boric anhydride, uses for this reagent include: fluxing agent for glass and enamels; starting material for synthesizing other boron compounds; additive in glass fibres (optical fibres); production of heat and/or chemical resistant borosilicate glass; as the inert capping layer in the production of gallium arsenide. In the present invention, it is believed that it may act as a catalyst. Also, Boron trioxide plays a role by allowing the other chemicals of the composition to come together. In addition, it is believed that it causes the chemicals to react, allowing the reaction to be observed under UV lighting. According to an embodiment, the boric anhydride may be present at about 0.004% w/v to about 0.035% w/v, or from about 0.004% w/v to about 0.0045%, or from about 0.0085% w/v to about 0.012%, or from about w/v 0.03% w/v-0.035% w/v of the composition, or about 0.004% w/v or about 0.03% w/v or about 0.01% w/v.

Potassium (K)—Potassium is a chemical element with symbol K (from Neo-Latin kalium) and atomic number 19. Elemental potassium is a soft silvery-white alkali metal that oxidizes rapidly in air and is very reactive with water, generating sufficient heat to ignite the hydrogen emitted in the reaction and burning with a lilac flame. Naturally occurring potassium is composed of three isotopes, one of which, $^{40}K$, is radioactive. Traces (0.012%) of this isotope are found in all potassium making it the most common radioactive element in the human body and in many biological materials, as well as in common building substances such as concrete. In the present invention, it is believed that it may act as a catalyst.

Magnesium oxide (MgO)—Chemically, magnesium oxide is a catalyst and starting point for the production of other magnesium salts. In addition, it is an acid acceptor finding applications in plastics manufacture and rubber compounding, and in acid neutralization in uranium, gallium, boron, lubricating oils and in reducing corrosion in boilers for example. In construction, it is a raw material in making cements used in flooring, wallboard, fibre board, tile and in steel coating. It is used in the manufacture of glass and fiberglass. It is a relatively poor desiccant, but because it neutralizes sulfur dioxide acids created by oxidation of Kraft-processed papers, it is used in libraries for book preservation. In the present invention, it is believed that it may act as a catalyst. According to an embodiment, the magnesium oxide may be present at about 0.0035% to about 0.035%, or from about 0.0035% w/v-0.0045% w/v of the composition, and preferably 0.004% w/v, or from about 0.025% w/v-0.035% w/v of the composition, preferably 0.03% w/v. According to another embodiment, the MgO may be present at about.

Gallium (III) oxide ($Ga_2O_3$)—Gallium (III) oxide is an important functional material. It is used in vacuum deposition and as part of the manufacturing of semiconductor devices. It has been studied in the use of lasers, phosphors and luminescent materials, has been shown to demonstrate catalytic properties and has also been used as an insulating barrier in tight junctions. Stable monoclinic $\beta$-$Ga_2O_3$ has current applications in gas sensors and luminescent phosphors and can be applied to dielectric coatings for solar cells. This oxide has also shown potential for deep-ultraviolet transparent conductive oxides. It is needed in the preparation of $Ga_2O_3$—$Al_2O_3$ catalyst. In the present invention, it is believed that it may act as a catalyst. According to an embodiment, the Gallium (III) oxide may be present at about 0.0025% w/v-0.017% w/v, or about 0.0025%-0.0035 w/v, or from about w/v-0 0.013% w/v-0.017% w/v of the composition, or about 0.003% w/v or about 0.015% w/v.

Nickel (II) oxide (NiO)—Nickel oxide is used in the production of alloys. It is used in the ceramic industry to make frits, ferrites, and porcelain glazes. This particular nickel oxide was also a component in the nickel-ion battery, also known as the Edison Battery, and is a component in fuel cells. It is a precursor to many nickel salts for use as specialty chemicals and catalysts. It has been studied as a counter electrode with tungsten oxide in complementary electrochromic devices. NiO is a versatile hydrogenation catalyst. Long-term inhalation of NiO is damaging to the lungs, causing lesions and in some cases, cancer. In the present invention, it is believed that it may act as a catalyst. According to an embodiment, the NiO may be present at about 0.0041% w/v-0.055%, or from about w/v 0.0041%-0.0057% w/v, or about 0.045% w/v-0.055% w/v of the composition, or about 0.005% w/v, or about 0.05% w/v.

Vanadium (V) oxide ($V_2O_5$)—Also known as vanadia and commonly known as vanadium pentoxide, it is a brown/yellow solid, although when freshly precipitated from aqueous solution, its color is deep orange. Vanadia, or vanadium (V) oxide, is predominantly used in the production of ferrovanadium, which primarily goes into the production of steel alloys. Another important use of vanadium (V) oxide is as a catalyst, most notably in the manufacture of sulfuric acid, polyester and alkyd resins, and phthalic anhydride, a precursor to plasticizers, used for conferring pliability to polymers. Due to its high coefficient of thermal resistance, vanadium (V) oxide finds use as a detector material in bolometers and microbolometer arrays for thermal imaging and as an ethanol sensor. Vanadium redox batteries are a type of flow battery used for energy storage, such as large power facility wind farms. Vanadium (V) oxide exhibits modest toxicity to humans, with a greater hazard when it is inhaled in the form of dust. According to an embodiment, the vanadium (V) oxide may be present at about 0.005% w/v-0.055% w/v, or about 0.005% w/v-0.006% w/v, or about 0.021% w/v-0.029% w/v, or about 0.045% w/v-0.055% w/v of the composition, or about 0.005 or about 0.05% w/v.

Bismuth Carbonate Oxide [$Bi_2O_2(CO_3)$]—Also known as bismuth subcarbonate, this substance is highly radiopaque. It finds use as filler in radiopaque catheters which can be seen by x-ray. In the 1930s, it was used as a constituent of milk of bismuth, a popular digestive tract cure-all. In modern medicine, it has been made into nanotube arrays that exhibit antibacterial properties. It is also used in fireworks. According to an embodiment, the bismuth carbonate oxide may be present at about 0.009% w/v-0.035% w/v, or about 0.009% w/v-0.013% w/v, or about 0.025% w/v-0.035% w/v of the composition, or about 0.011, or about 0.03% w/v.

Bismuth Chloride Oxide (BiClO)—Also known as bismuth oxychloride, this substance is a lustrous white solid used since antiquity as a cosmetic. It has a pearly, iridescent quality which lends itself to use as an ingredient in eye shadow, hair spray, powders, nail polishes and other cosmetic products. According to an embodiment, the bismuth chloride oxide may be present at about 0.0085% w/v-0.011% w/v of the composition, and preferably 0.01% w/v.

Bismuth Oxide ($Bi_2O_3$)—$\delta$-$Bi_2O_3$ has been investigated for solid-oxide fuel cells due to it being principally an ionic conductor. Bismuth oxide is occasionally used in dental materials to make them more opaque to X-rays than the surrounding tooth structure. In particular, it has been used in hydraulic silicate cements for use in various dental procedures. However, it has been claimed that it can caused discolouration over time with exposure to light or reaction with other materials in the tooth treatment, such as sodium hypochlorite. According to an embodiment, the bismuth oxide may be present at about 0.013% w/v-0.017% w/v, or about 0.015% w/v.

Cesium bromide (CsBr)—Cesium is used in industry as a catalyst promoter, for boosting the performance of other metal oxides in the capacity and for the hydrogenation of organic compounds. Cesium salts are used to strengthen various types of glass. Cesium halides such as bromide (as well as chloride and iodide) crystallize in a simple cubic crystal system, also referred to as the "cesium chloride structure" which is a structure that is preferred to those of most other alkaline halides, which adopt the sodium chloride structure. The cesium chloride structure is composed of a primitive cubic lattice with a two-atom basis, each with an eightfold coordination; the chloride atoms lie upon the lattice points at the edges of the cube, while the cesium atoms lie in the holes in the center of the cubes. Other cesium compounds are used in optical glasses, optical instruments and increasing sensitivity of electron tubes. According to an embodiment, the cesium bromide may be present at about 0.003% w/v-0.0047% w/v, or about 0.015% w/v.

Lanthanum (III) oxide (La$_2$O$_3$)—Lanthanum (III) oxide or lanthanum oxide (La$_2$O$_3$) is used to make optical glasses, increasing density, refractive index and hardness. With oxides of tungsten, tantalum and thorium, lanthanum oxide improves the resistance of the glass to attack by alkali. Lanthanum oxide is used in the manufacture of piezoelectric and thermoelectric materials. Catalytic converters contain lanthanum oxide. It is also used in x-ray imagining intensifying screens, phosphors as well as dielectric and conductive ceramics. Lanthanum oxide was also examined as a catalyst for the oxidative coupling of methane. According to an embodiment, the lanthanum (III) oxide may be present at about 0.00388% w/v-0.0055% w/v, or about 0.00456% w/v.

Molybdenum (VI) oxide (MoO$_3$)—Molybdenum (VI) oxide or molybdenum trioxide is used in the manufacture of molybdenum metal. The metal is an additive to steel and corrosion-resistant alloys. Molybdenum trioxide is also a co-catalyst used in the production of acrylonitrile. It is of interest in electrochemical devices and displays. When it comes in contact with water, it forms hydrogen ions that can kill bacteria effectively, making it a potential anti-microbial agent. According to an embodiment, the (VI) oxide may be present at about 0.004% w/v-0.025% w/v, or about 0.004% w/v-0.0006% w/v, or about 0.019% w/v-0.025% w/v, or about 0.022% w/v or about 0.0045% w/v.

Neodymium oxide (Nd$_2$O$_3$)—Neodymium oxide (Nd$_2$O$_3$) is used to dope glass. It is used to make solid-state laser and to color glasses and enamels. It is used in sunglasses and welding goggles. Some neodymium-doped glass is dichroic, changing color depending on the lighting. Neodymium oxide is also used as a polymerization catalyst. According to an embodiment, the Neodymium oxide may be present at about or about 0.0048% w/v-0.032% w/v, or about 0.0048% w/v-0.0065% w/v, or about 0.024% to about 0.032% w/v, or about 0.028% w/v, or about 0.0056% w/v.

Nickel (II) carbonate anhydrous (NiCO)—Nickel (II) carbonate is an intermediate in the hydrometallurgical purification of nickel from its ores and is used in electroplating of nickel. Nickel carbonates are also used in some ceramic applications and as precursors to catalysts. According to an embodiment, the nickel (II) carbonate may be present at about or about 0.007% w/v-0.01% w/v, or about 0.008% w/v.

Pigments

A pigment is a material that changes the color of reflected or transmitted light as the result of wavelength-selective absorption. This physical process differs from fluorescence, phosphorescence, and other forms of luminescence, in which a material emits light. Many materials selectively absorb certain wavelengths of light. Materials that humans have chosen and developed for use as pigments usually have special properties that make them ideal for coloring other materials. A pigment must have a high tinting strength relative to the materials it colors.

According to an embodiment, the composition of the present invention comprises a number of chemical compounds which act as pigmentsas follows.

Antimony (V) oxide (Sb$_2$O$_5$)—Also known as antimony pentoxide, it finds uses as a flame retardant in ABS and other plastics, a flocculant in the production of titanium dioxide and is sometimes used in the production of glass and adhesives. In paint it is used as a pigment. It is also used as an ion-exchange resin for a number of cations in acidic solution and as a polymerization and oxidation catalyst. The antimony (V) oxide may be present at about 0.005% w/v to about 0.017% w/v, or from about 0.005% w/v to about 0.007% w/v, or about 0.013% w/v-0.017% w/v of the composition, or about 0.006% w/v or about 0.015% w/v.

Scandium (III) oxide (Sc$_2$O$_3$)—Also known as scandia, it is a high melting rare earth oxide. It is used in the preparation of other scandium compounds as well as in high-temperature systems (for its resistance to heat and thermal shock), electronic ceramics, and glass composition (as a helper material). According to an embodiment, the scandia may be present at about 0.0035% w/v-0.023% w/v, or about 0.0035% to about 0.0045% w/v, to about 0.017% w/v-0.023% w/v of the composition, and about 0.004% w/v of about 0.02% w/v.

Lead (IV) oxide (PbO$_2$)—Also known as lead dioxide, it is used in the production of matches, pyrotechnics, dyes and the curing of sulfide polymers. It is also used in the construction of high-voltage lightning arresters. The most important use of lead dioxide is as the cathode of lead acid batteries. It was once used as anode material in electrochemistry. According to an embodiment, the lead (IV) oxide may be present at about 0.0045% w/v-0.065% w/v, or from about 0.0045% w/v-0.0065% w/v, or from about 0.045% w/v-0.065% w/v of the composition, or about 0.0055% w/v or about 0.055% w/v.

Lead (II) oxide (PbO)—Lead (II) oxide or lead monoxide is mostly used in lead-based industrial glass and industrial ceramics, including computer components. Other applications include vulcanization of rubber and the production of certain pigments and paints. It remains the key component of automotive lead-acid batteries. Lead oxide may be fatal is swallowed or inhaled and can bioaccumulate in plants and mammals. According to an embodiment, the lead (II) oxide may be present at about 0.0045% w/v-0.065% w/v, or from about 0.0045% w/v-0.0065% w/v, or from about 0.027% w/v-0.036% w/v or from about 0.045% w/v-0.065% w/v of the composition, or about 0.0055% w/v, or about 0.031% w/v, or about 0.055% w/v.

Sulfur Powder (S)—Elemental sulfur is mainly used as a precursor to other chemicals, and mostly for the manufacture of sulfuric acid. Sulfuric acid is principally used in the extraction of phosphate ores for fertilizer manufacturing, but is also used in oil refining, wastewater processing and mineral extraction. Sulfur is used to vulcanize rubber and is a component in gunpowder. Other sulfur compounds are used in the manufacture of cellophane and rayon, in bleaching paper and in preservation of wine and certain foods, such as dried fruit. Many surfactants and detergents are sulfate derivatives. Calcium sulfate is used in Portland cement, the most common type of cement in general use around the world. Organosulfur compounds are used in pharmaceuticals, dyestuffs and agrochemicals. Elemental sulfur is one of the oldest fungicides and pesticides. According to an embodiment, the sulfur powder may be present at about 0.045% w/v-0.065% w/v of the composition, and preferably 0.055% w/v.

Tungsten (VI) oxide (WO$_3$)—Tungsten (VI) oxide, or tungsten trioxide, is frequently used to manufacture tungstates for x-ray screen phosphors, for fireproofing fabrics and in gas sensors. It is also used as a pigment in ceramics and paints. It has been used in the production of electrochromic (smart) windows which allow the user to adjust the tint of the windows with the application of voltage, light or heat. As an ingredient in photocatalytic tungsten (VI) oxide/noble metal composites, the composites show a modest hydrogen production performance. According to an embodiment, the Tungsten (VI) oxide may be present at about 0.004% w/v-0.07% w/v, or about 0.004% w/v-0.006% w/v or about 0.05% w/v-0.07% w/v of the composition, or about 0005% w/w or about 0.06% w/v.

Chromium (III) oxide ($Cr_2O_3$)—Because of its green color and considerable stability, chromium (III) oxide has been commonly used as a pigment. It is used in paints, inks and glasses. It is also one of the materials used when polishing the edges of knives, razors, etc. on a piece of leather, balsa, cloth or other material. According to an embodiment, the chromium (III) oxide may be present at about 0.0045% w/v-0.006% w/v, or about 0.005% w/v.

Copper (II) oxide or cupric oxide (CuO)—It is a black solid that is a product of copper mining and the starting point for the production of other copper salts as well as many wood preservatives. Cupric oxide finds use as a pigment in ceramics to produce blue, red, green and sometimes gray, pink or black glazes. It is a dietary supplement in animals. It is used in welding with copper alloys and it can be used to safely dispose of hazardous materials such as cyanide, hydrocarbons, halogenated hydrocarbons and dioxins through oxidation. According to an embodiment, the copper (II) oxide may be present at about 0.0038% w/v-0.0051% w/v, or about 0.0045% w/v.

Copper (I) oxide ($Cu_2O$)—Also known as cuprous oxide, this compound is used as a pigment, fungicide and antifouling agent for marine paints. Copper (I) oxide is responsible for the pink colour in a positive Benedict's test for the presence of reducing sugar(s). According to an embodiment, the copper (I) oxide may be present at about 0.02% w/v-0.041% w/v, or about 0.25, or about 0.035% w/v.

Iron (III) oxide or Ferric oxide ($Fe_2O_3$)—This oxide of iron is the main source of iron for the steel industry. As a very fine powder, it is known as "jeweller's rouge," used to put the final polish on metallic jewellery and lenses, or as a stropping compound to assist in getting a razor edge on knives, straight razors or any other edged tool. Ferric oxide is also used as pigments, some of them FDA-approved for used in cosmetics. $\alpha$-$Fe_2O_3$ has been studied as a photoanode for the water-splitting reaction. Iron (III) oxide (about 0.5%) is mixed with zinc oxide to create calamine, the active ingredient in calamine lotion. According to an embodiment, the iron (III) oxide may be present at about 0.005% w/v-0.006% w/v, or about 0.005% w/v.

Additional Ingredients

The composition of the present invention comprises additional ingredients including:

Calcium fluoride precipitated ($CaF_2$)—Calcium fluoride ($CaF_2$) in the fluorite state is a significant fluoride source. It is a principal ingredient in the manufacture of hydrogen fluoride, which is used to produce a wide range of materials. Calcium fluoride is also used to manufacture optical components such as windows and lenses, used in thermal imaging systems, spectroscopy, and excimer lasers. Its low refractive index eliminates the need for anti-reflection coatings. According to an embodiment, the calcium fluoride may be present at about 0.012% w/v-0.03% w/v, or about 0.012%, or about 0.025% w/v.

Tin (powder-Sn)—One half of the tin produced in the world in 2006 was for use in solder. Tin readily bonds to iron, and is therefore used in coating steel to prevent corrosion. Tin is also used in the production of alloys such as pewter, bronze and zirconium alloys. A niobium-tin compound is used commercially as wires for superconducting magnets, due to the material's high critical temperature and critical magnetic field. A tin-lead alloy is used in the manufacture of the pipes in a pipe organ, as tin is a tonally resonant metal. Tin has been used in Li-ion batteries. Tin fluoride is added to some dental care products. Organotin compounds are used in the stabilization of PVC plastics. Organotin compounds can have relatively high toxicity: they have been used for their biocidal effects in fungicides, pesticides, algaecides, wood preservatives and antifouling agents. Tin reagents are useful in organic chemistry. According to an embodiment, the tin may be present at about 0.003% w/v-0.0005% w/v, or about 0.004% w/v.

Tellurium (IV) oxide ($TeO_2$)—Tellurium (IV) oxide, or tellurium dioxide, is used as an acousto-optic material. It is also used as a conditional glass former. It will form glass with small molar percentage additions of an oxide or halide, for example. Tellurium dioxide glasses have a high refractive index and transmit into the mid-infrared part of the electromagnetic spectrum, making them of technological interest for optical waveguides. Tellurite glasses exhibit Raman gain up to 30 times that of silica, making them useful in optical fibre amplification. According to an embodiment, the tellurium oxide may be present at about 0.0039% w/v-0.0053% w/v, or about 0.0046% w/v.

Zirconium (IV) oxide [nanopowder-($ZrO_2$)]—The main use of zirconium (IV) oxide or zirconia ($ZrO_2$) is in the production of ceramics. It is used as a protective coating on particles of titanium dioxide pigments, as a refractory material, in insulation, abrasives and enamels. Stabilized zirconia is used in oxygen sensors and fuel cell membranes due to its ability to allow oxygen ions to move freely through the crystal structure at high temperatures. With its high ionic conductivity and low electronic conductivity, it is one of the most useful electroceramics. It is used as the solid electrolyte in electrochromic devices. With very low thermal conductivity of cubic phase of zirconia, it has also been used as a thermal barrier coating, particularly in jet and diesel engines to allow operation at higher temperatures. This property also lends use in ceramic fibre insulation for crystal growth furnaces, fuel cell stack insulation and infrared heating systems. Zirconia is a potential high-k dielectric material with potential applications as an insulator in transistors. It is also being employed in optical coatings due to its low absorption from near-UV to mid-infrared. Other uses include diamond simulation in jewellery. It is being used in the construction of dental restorations. Zirconia knives stay sharp longer than stainless steel ones. Historically, zirconia was an ingredient in limelight due to its infusibility and luminosity when incandescent. According to an embodiment, the zirconium (IV) oxide may be present at about 0.004% w/v-0.04% w/v, or at about 0.004% w/v 0.0005% w/v, or 0.03% w/v-0.04% w/v, or about 0.035% w/v, or about 0.0045% w/v.

Without wishing to be bound by theory, the inventors believe that the components of the screening composition of the present invention will interact with one or more molecule in the substance and provide information as to the possibility of causing an adverse reaction if ingested.

pH Adjusting Agent

The composition of the present invention may also comprise a pH adjusting agent to bring the composition to the desired pH.

Any suitable pH adjusting agent may be used in the present invention. Known suitable pH adjusting agents include but are not limited to Acetic Acid, Adipic Acid, Ammonium Aluminum Sulphate, Ammonium Bicarbonate, Ammonium Carbonate, Ammonium Citrate, dibasic, Ammonium Citrate, monobasic, Ammonium Hydroxide, Ammonium Phosphate, dibasic, Ammonium Phosphate, monobasic, Calcium Acetate, Calcium Acid Pyrophosphate, Calcium Carbonate, Calcium Chloride, Calcium Citrate, Calcium Fumarate, Calcium Gluconate, Calcium Hydroxide, Calcium Lactate, Calcium Oxide, Calcium Phosphate, dibasic, Calcium Phosphate, monobasic, Calcium Phosphate, tribasic, Calcium Sulphate, Carbon Dioxide, Citric Acid, Cream of Tartar, Fumaric Acid, Gluconic Acid, Glucono-delta-lactone, Hydrochloric Acid, Lactic Acid, Magnesium Carbonate, Magnesium Citrate, Magnesium Fumarate, Magnesium Hydroxide, Magnesium Phosphate, Magnesium Sulphate, Malic Acid, Manganese Sulphate, Metatartaric Acid, Phosphoric Acid, Potassium Acid Tartrate, Potassium Aluminum Sulphate, Potassium Bicarbonate, Potassium Carbonate, Potassium Chloride, Potassium Citrate, Potassium Fumarate, Potassium Hydroxide, Potassium Lactate, Potassium Phosphate, dibasic, Potassium Sulphate, Potassium Tartrate, Sodium Acetate, Sodium Acid Pyrophosphate, Sodium Acid Tartrate, Sodium Aluminum Phosphate, Sodium Aluminum Sulphate, Sodium Bicarbonate, Sodium Bisulphate, Sodium Carbonate, Sodium Citrate, Sodium Fumarate, Sodium Gluconate, Sodium Hexametaphosphate, Sodium Hydroxide, Sodium Lactate, Sodium Phosphate, dibasic, Sodium Phosphate, monobasic, Sodium Phosphate, tribasic, Sodium Potassium Tartrate, Sodium Pyrophosphate, tetrabasic, Sodium Tripolyphosphate, Sulphuric Acid, Sulphurous Acid, Tartaric Acid, lithium carbonate, magnesium hydroxide carbonate. Preferably, the pH adjusting agent is potassium carbonate, magnesium carbonate, lithium carbonate, magnesium hydroxide carbonate or combinations thereof.

According to an embodiment, the potassium carbonate may be present at 0.0045% w/v-0.06% w/v, or from about 0.0045% w/v-0.006% w/v or from about 0.045% w/v-0.006% w/v of the composition, or about 0.005% w/v, or about 0.05% w/v.

According to an embodiment, the magnesium carbonate may be present at 0.04% w/v-0.05% w/v of the composition, preferably 0.045% w/v.

According to an embodiment, the calcium carbonate may be present at 0.0045% w/v-0.006% w/v of the composition, preferably 0.005% w/v.

According to an embodiment, the lithium carbonate may be present at 0.024% w/v-0.034% w/v of the composition, preferably 0.029% w/v.

According to an embodiment, the magnesium hydroxide carbonate may be present at 0.005% w/v-0.05% w/v, or at about 0.005% w/v-0.007% w/v, or at about 0.04% w/v-0.05% w/v of the composition, or about 0.006% w/v, or about 0.045% w/v.

According to an embodiment, the sodium bicarbonate may be present at 0.0189% w/v-0.0256% w/v of the composition, preferably 0.0222% w/v.

Potassium carbonate ($K_2CO_3$)—According to an embodiment, potassium carbonate, which is a chemical compound with the formula $K_2CO_3$, may be used in the present invention as a compound to facilitate the formation of bonds between the components of the formulations. Potassium carbonate ($K_2CO_3$) is a white salt, soluble in water (insoluble in ethanol), which forms a strongly alkaline solution. It can be made as the product of potassium hydroxide's absorbent reaction with carbon dioxide. It is deliquescent, often appearing a damp or wet solid. Potassium carbonate is used in the production of soap and glass.

Magnesium carbonate ($MgCO_3$)—The primary use of magnesium carbonate is in the production of magnesium oxide. It is also used in flooring, fireproofing, fire extinguishing compositions, cosmetics, dusting powder, and toothpaste. Other applications are as filler material, smoke suppressant in plastics, a reinforcing agent in neoprene rubber, a drying agent, a laxative, and colour retention in foods. High purity magnesium carbonate is used as antacid. Because of its hygroscopic qualities, it is used as an additive to table salt to help keep it free-flowing and also by certain athletes as a drying agent for hands in rock climbing, gymnastics and weight lifting.

Magnesium hydroxide carbonate ($C_2H_2Mg_3O_8$)—Magnesium carbonate is primarily used in the production of magnesium oxide. It is used in flooring, fireproofing, fire extinguishing compositions, cosmetics, dusting powder and toothpaste. It is also used as filler material, smoke suppressant in plastics, reinforcing agent in neoprene rubber, drying agent, laxative and colour retention in foods. High purity magnesium carbonate is used as antacid. Because of its hygroscopic qualities, it is used as an additive to table salt to help keep it free-flowing and also by certain athletes as a drying agent for hands in rock climbing, gymnastics and weight lifting. According to an embodiment, the magnesium hydroxide carbonate may be used at about 0.0047% w/v-0.00066% w/v of the composition, and preferably 0.00575% w/v.

Lithium carbonate ($Li_2CO_3$)—In addition to its use in the treatment of bipolar disorder, lithium carbonate is an important industrial chemical. It forms low-melting fluxes with silica and other materials. It is a common ingredient in both low-fire and high-fire ceramic glaze and finds use in ovenware glasses. Cement sets quicker when prepared with lithium carbonate. It is useful for tile adhesives. It can be used in the processing of aluminum. It is also used in the manufacture of most lithium-ion batteries.

Screening Strip

According to another embodiment, the screening strip of the present invention may comprise a solid phase layer, comprising an adsorbent, and a screening composition of the present invention.

The solid phase layer may be any suitable material onto which an adsorbent may be deposited. For example, the material may be a plastic material, a polymeric material, a natural fiber material such as a paper filter, filter membranes such as nylon, cellulose, nitrocellulose, PVDF materials or the likes. The material may also be a glass material.

Adsorbent

The solid support material used in the present invention may also comprise an adsorbent, that is, a substance that adsorbs another, Adsorption is the adhesion of atoms, ions, or molecules from a gas, liquid, or dissolved solid to a surface. This process creates a film of the adsorbate on the surface of the adsorbent. This process differs from absorption, in which a fluid (the absorbate) permeates or is dissolved by a liquid or solid (the absorbent). Adsorption is a surface-based process while absorption involves the whole volume of the material. The term sorption encompasses both processes, while desorption is the reverse of it. Adsorption is a surface phenomenon.

According to an embodiment, the adsorbent may be for example a silica gel ($SiO_2$), titanium dioxide ($TiO_2$), an aluminum oxide, Strontium titanate ($SrTiO_3$), or a cellulose. According to an embodiment, the silica gel may be used at about 0.475% w/v-0.625% w/v of the composition, and preferably 0.55% w/v. According to an embodiment, the silica gel may be used at about 0.475% w/v-0.625% w/v of the composition, and preferably 0.55% w/v.

According to an embodiment, a preferred adsorbent is silica gel, which is a granular, vitreous, porous form of silicon dioxide made synthetically from sodium silicate. Silica gel is tough and hard; it is more solid than common household gels like gelatin or agar. It is a naturally occurring mineral that is purified and processed into either granular or beaded form. As a desiccant, it has an average pore size of 2.4 nanometers and has a strong affinity for water molecules.

According to an embodiment, another preferred adsorbent is titanium dioxide ($TiO_2$). Titanium dioxide, also known as titanium (IV) oxide or titania, is the naturally occurring oxide of titanium, chemical formula $TiO_2$. When used as a pigment, it is called titanium white, Pigment White 6 ($PW_6$), or CI 77891. Generally it is sourced from ilmenite, rutile and anatase. It has a wide range of applications, from paint to sunscreen to food colouring. When used as a food coloring, it has E number E171. The main use of titanium dioxide in industry is as a white powder pigment. It is resistant to discoloration under ultraviolet light exposure. This powder is found in paints and coatings including glazes and enamels, plastics, paper, inks, fibers, foods, pharmaceuticals and cosmetics. There is growing use of titanium dioxide in toothpastes and sunscreen. Because of its oxidative and hydrolysis properties, its demand is growing in photocatalysts, with applications including light-emitting diodes, LCDs and electrodes for plasma displays. When exposed to UV light, titanium dioxide becomes increasingly hydrophilic and can be used for anti-fogging coatings and self-cleaning windows. Its disinfecting properties find use in medical devices, food preparation surfaces, air conditioning filters and sanitary ware surfaces. It can also be used as an oxygen sensor. According to an embodiment, the titanium dioxide may be present at about 30% w/v-35% w/v of the composition, or 30%, 31%, 32%, 33%, 34%, 35% w/v.

According to an embodiment, the titanium oxide may be for example BASF® Aurasperse W-318 Titanium White™.

According to another embodiment, the adsorbent may be aluminum oxide ($Al_2O_3$). It is widely used to remove water from gas streams, or absorb excess moisture from the filter paper used in the present invention. According to an embodiment, the aluminum oxide may be present at about 0.045% w/v-0.065% w/v of the composition, and preferably 0.055% w/v.

Strontium titanate ($SrTiO_3$)—This oxide of strontium and titanium was, at one time, produced for the sole purpose of simulating diamond until better substitutes were found. In embodiments of the present invention, strontium titanate is used as an adsorbent to remove the excess moisture from the filter paper used in the present invention. According to an embodiment, the strontium titanate may be present at about 0.01% w/v-0.014% w/v of the composition, and preferably 0.012% w/v.

Solvents may be used to dissolve the adsorbent and apply the adsorbent on the solid support (on the surface thereof, on soaked through the entirety of the solid support). A solvent is a substance that dissolves a solute (a chemically different liquid, solid or gas), resulting in a solution. Suitable solvents that may be used in the present invention include organic solvents, such as for example acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethyl ether, diethylene glycol, diglyme (diethylene glycol dimethyl ether), 1,2-dimethoxy-ethane (glyme, DME), dimethylether, dimethylformamide (DMF), dimethyl sulfoxide (DMSO), dioxane, ethanol, ethyl acetate, ethylene glycol, glycerin, heptane, Hexamethylphosphoramide (HMPA), Hexamethylphosphorous, triamide (HMPT), hexane, methanol, methyl t-butyl ether (MTBE), methylene chloride, N-methyl-2-pyrrolidinone (NMP), nitromethane, pentane, Petroleum ether (ligroine), 1-propanol, 2-propanol, pyridine, tetrahydrofuran (THF), toluene, triethyl amine, water, water, heavy, o-xylene, m-xylene, p-xylene. Preferably, the solvent is water.

According to an embodiment, the composition of the present may be applied to filter paper to create a strip test ready to receive the body fluid (e.g. saliva). Different groups of chemicals making up the composition of the present invention may be successively applied to the filter paper. Once the chemicals have been applied in the proper order to the filter paper, and completely dried, the test strip is ready to receive the body fluid. According to an embodiment, the interaction of the body fluid with the test strip is then immediately observable in a dark room under ultraviolet light (black light).

Based on reaction of the substance with the composition and/or strip test thereof, the test will conclude if the substance tested would have deleterious effect on a person. Ultimately, the primary benefit of this screening composition of the present invention is to allow science to expand its knowledge in the chemistry of these substances.

According to an embodiment, there is disclosed a method of screening substance comprising contacting a composition of the present invention, or a screening strip of the present invention, with a substance dissolved in a solvent. The composition and/or the screening strip are then exposed to UV light in the dark, and the presence or absence of toxicity is confirmed by the fluorescence of the composition and/or screening strip, or the absence thereof. According to an embodiment, the presence of fluorescence is indicative of an absence or reduced toxicity, and the absence of fluorescence is indicative of the presence or increased toxicity. The intermediary degrees of fluorescence may be used to gauge the degree of toxicity of the substance being tested.

According to another embodiment, there is disclosed a method of screening for a sensitivity, intolerance or allergy to chemical substances comprising the steps of:
  a) contacting a screening composition of claim 1, or a screening strip of claim 10 with a chemical substance;
  b) measuring and comparing a fluorescence level from said screening composition or said screening strip contacted with said bodily fluid of said subject to a positive and/or negative control body fluid samples;
wherein a fluorescence level comparable to said negative control is indicative of an absence of sensitivity, intolerance or allergy;
wherein a fluorescence level intermediate to said negative control and said positive control is indicative of an intermediate level of sensitivity, intolerance or allergy; and
wherein absence of fluorescence is indicative of an presence of sensitivity, intolerance or allergy.

According to another embodiment, there is disclosed a method of screening for a sensitivity, intolerance or allergy to chemical substances in a subject comprising the steps of:
  a) contacting a screening composition of claim 1, or a screening strip of claim 10 with a bodily fluid of said subject;
  b) measuring and comparing a fluorescence level from said screening composition or said screening strip contacted with said bodily fluid of said subject to a positive and/or negative control body fluid samples;
  wherein a fluorescence level comparable to said negative control is indicative of an absence of sensitivity, intolerance or allergy;
  wherein a fluorescence level intermediate to said negative control and said positive control is indicative of an intermediate level of sensitivity, intolerance or allergy; and
  wherein absence of fluorescence is indicative of an presence of sensitivity, intolerance or allergy.

As used herein, the term "measuring" is intended to mean a simple visual assessment of the present or absence or fluorescence. In another embodiment, "measuring" is also intended to mean detecting the fluorescence with an appropriate apparatus (e.g. a luminometer) to obtain a numerical value from said apparatus, for each sample and/or substance, as well as control samples being tested.

As used herein, the term "comparing" is intended to mean a simple visual comparison of the present or absence or fluorescence between the tested sample and/or substance being tested and the included control samples. It is also intended to mean a comparison of the measured numerical values in their raw form or in transformed (e.g. normalized) form, and/or the numerical values from which background fluorescence from a no treatment control has been subtracted, for example. In this context, a fluorescence level comparable to the negative control is indicative of an absence of sensitivity, intolerance or allergy, a fluorescence level intermediate to the negative control and the positive control is indicative of an intermediate level of sensitivity, intolerance or allergy; and absence of fluorescence is indicative of an presence of sensitivity, intolerance or allergy.

The method of the present invention may further comprise the step of discontinuing use of the chemical substance, continuing use of the chemical substance, or increasing or decreasing the level of use of said chemical substance based on result of the method.

The method may further comprise the step a") prior to performing said method:
  a") obtaining a bodily fluid from said subject prior to use of said chemical substance.

The method may further comprise the step a') prior to performing said method:
  a') obtaining a bodily fluid from said subject after use of said chemical substance.

The method may further comprise contacting the screening composition or the screening strip contacted with the bodily fluid of the subject with an activator composition prior to step b).

The activator composition comprises:
  from about 0.44% to about 0.47% w/v iodine;
  from about 0.009% to about 0.013% w/v bismuth carbonate oxide;
  from about 0.0005% to about 0.0066% w/v magnesium hydroxide carbonate;
  from about 0.007% to about 0.01% w/v nickel (II) carbonate;
  from about 0.0039% to about 0.0053% w/v tellurium oxide; and
  from about 0.0035% to about 0.005% w/v cesium bromide.

The activator composition may also comprises:
  from about 0.44% to about 0.47% w/v iodine;
  from about 0.012% to about 0.016% w/v bismuth carbonate oxide;
  from about 0.019% to about 0.026% w/v sodium bicarbonate;
  from about 0.02% to about 0.027% w/v copper (I) oxide;
  from about 0.02% to about 0.03% w/v calcium fluoride; and from about 0.0009% to about 0.0012% w/v magnesium oxide.

The present invention will be more readily understood by referring to the following examples which are given to illustrate the invention rather than to limit its scope.

EXAMPLE 1

Screening Composition 1

The baseline formulation "A" is prepared by mixing the listed ingredients according to the method described below in example 3. The quantities and concentrations are shown as the preferred quantity/concentration, and over a range of quantities and concentrations.

TABLE 1

Baseline for Positive Charge Strip Test "A" (for 100 ml of solution)

| Ingredient | Quantity | Concentration |
| --- | --- | --- |
| Gram's iodine solution | 93.50 ml | Iodine 0.33% (w/v) and potassium iodide 0.66% (w/v) in water |
| Antimony oxide | 0.03 g<br>0.026 g-0.034 g | 0.03% w/v<br>0.026% w/v-0.034% w/v |
| Magnesium oxide | 0.06 g<br>0.05 g-0.07 g | 0.06% w/v<br>0.05% w/v-0.07% w/v |
| Potassium carbonate | 0.10 g<br>0.09 g-0.10 g | 0.10% w/v<br>0.09% w/v-0.10% w/v |
| Magnesium carbonate | 0.09 g<br>0.08 g-0.10 g | 0.09% w/v<br>0.08% w/v-0.10% w/v |
| Lead oxide (IV) | 0.11 g<br>0.09 g-0.13 g | 0.11% w/v<br>0.09% w/v-0.13% w/v |
| Boric anhydride | 0.06 g<br>0.05 g-0.07 g | 0.06% w/v<br>0.05% w/v-0.07% w/v |
| Nickel oxide (II) | 0.10 g<br>0.09 g-0.11 g | 0.10% w/v<br>0.09% w/v-0.11% w/v |
| Gallium oxide (III) | 0.03 g<br>0.026 g-0.034 g | 0.03% w/v<br>0.026% w/v-0.034% w/v |
| Scandium oxide (III) | 0.04 g<br>0.034-0.046 g | 0.04% w/v<br>0.034% w/v-0.046% w/v |

TABLE 2

Extended for Positive Charge Strip Test "B" (for 100 ml)

| Ingredient | Quantity | Concentration |
| --- | --- | --- |
| Titanium dioxide slurry | 93.75 ml | 60-70% w/v |
| Sulfur powder | 0.11 g<br>0.09 g-0.13 g | 0.11% w/v<br>0.09% w/v-0.13% w/v |
| Aluminum oxide | 0.11 g<br>0.09 g-0.13 g | 0.11% w/v<br>0.09% w/v-0.13% w/v |
| Vanadium (V) oxide | 0.10 g<br>0.09 g-0.11 g | 0.10 g<br>0.09% w/v-0.11% w/v |
| Tungsten (VI) oxide | 0.12 g<br>0.10 g-0.14 g | 0.12% w/v<br>0.10% w/v-0.14% w/v |
| Fluorescein disodium salt | 0.21 g<br>0.18 g-0.24 g | 0.21% w/v<br>0.18% w/v-0.24% w/v |

EXAMPLE 2

Preparation of Test Strip Solid Phase Layer

TABLE 3

Ethanol and silica solution

| Ingredient | Quantity | Concentration |
| --- | --- | --- |
| Ethanol | 250 ml | 100% vol/vol |
| Silica gel | 1.1 g<br>0.95 g-1.25 g | 1.1% w/vol<br>0.95% w/v-1.25% w/v |

The ethanol and silica gel solution described above in table 3 is left to rest at room temperature, and a Whatman™ Qualitative Filter Paper Grade 3 (e.g. CAT No. 1003-110 or No. 1003-090) is allowed to soak for at least four hours.

When the soaking time is complete, the treated filter paper is removed and left to dry. After the filter is dried, the excess silica gel is brushed or blown off the filter paper.

After complete drying the filter paper, or strips cut therefrom may be used for screening purposes.

EXAMPLE 3

Preparation of the Screening Formulation

The chemicals in Table 1 and Table 2 are put together in the listed, sequential order disclosed above. Group A and B chemicals are mixed separately in a 250 ml beaker or equivalent container. Stirring of the solution is kept on, such that each new chemical added to the solution is immediately stirred and mixed with the other as it is added. After the chemicals have been mixed in sequential order, helium gas is added bubbled through the solution by barbotage for a period of 20 to 30 seconds. After the helium gas has been added, the mixture is stirred and is then placed under plant light {blue light [e.g. (~425-450 nm wavelength)] 75 W indoor plant light bulb or equivalent) to facilitate the homogenous mixing of the chemical mixtures and reaction together. This process involving the plant light takes approximately 10 to 15 minutes, after the solution is removed from the plant light.

When the chemicals of Group A and Group B have been prepared, the Group A chemicals solution is poured into the Group B solution respectively, and then stirred until homogenous (about 30 seconds). The mixture is then ready to be used for application to the filter solid support.

EXAMPLE 4

Preparation of Test Strips

The pre-treated Whatman filter paper prepared above is coated with the liquid screening formulation. Each strip test is coated with 3 layers of the liquid formulation, which are applied consecutively, after the previous layer has dried (after about 10 minutes).

Once the first application layer has been applied, the painted filter paper is placed under the same plant light for 30 minutes. After 30 minutes, another layer of paint is applied. It is then placed back under the same plant light for 30 minutes. After the second 30 minutes, a third layer of liquid solution is applied to the filter paper, giving it three equal coats. Upon completion of the third coat, the strip test is placed under the plant light to dry completely.

EXAMPLE 5

Screening Test Procedure

Prior to testing, the specimen of substance is placed directly into a solvent. Preferably, the solvent is a solvent such as distilled or filtered water. If the specimen is in tablet form, it should be crushed into a powder form and then added to the solvent. If the specimen is in other form, it is preferably disaggregated into smaller pieces. The powder or pieces are then left to sit in the solvent until dissolved, for a period ranging from a few second to minutes, hours or even days before it may be tested with the composition and/or strip test of the present invention. Preferably, the contact with the solvent is at least eight hours. A liquid or gel form can be put directly into the solvent. Any capsule contents can be put into the solvent without the encapsulation material. However, the actual capsule material by itself can also be tested.

Figure 1:
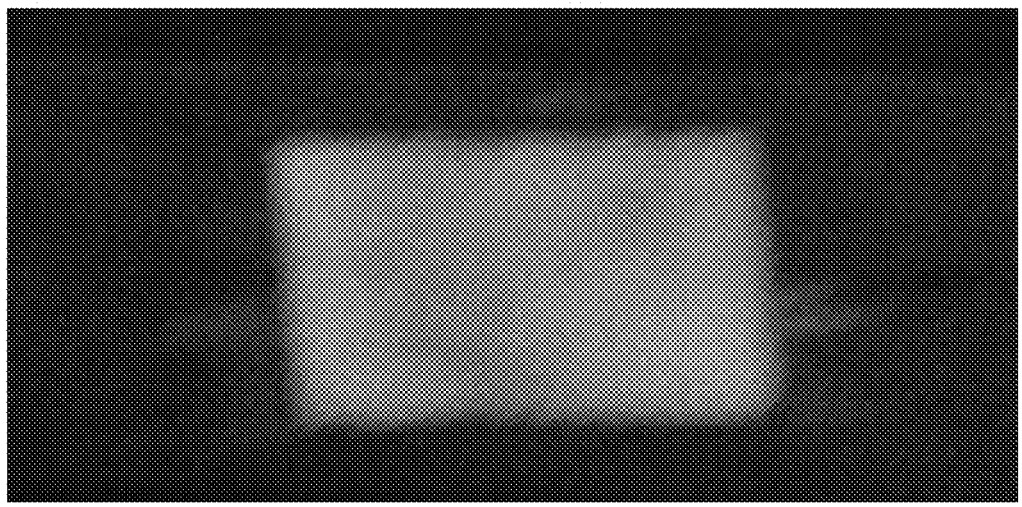
FIG. 1 illustrates a strip test according to the present invention that has been contacted with a sample of a substance that does not cause an adverse effect to an individual. The substance is a sample of the blood pressure medication. The test strip glows a bright yellow color.
Figure 2:
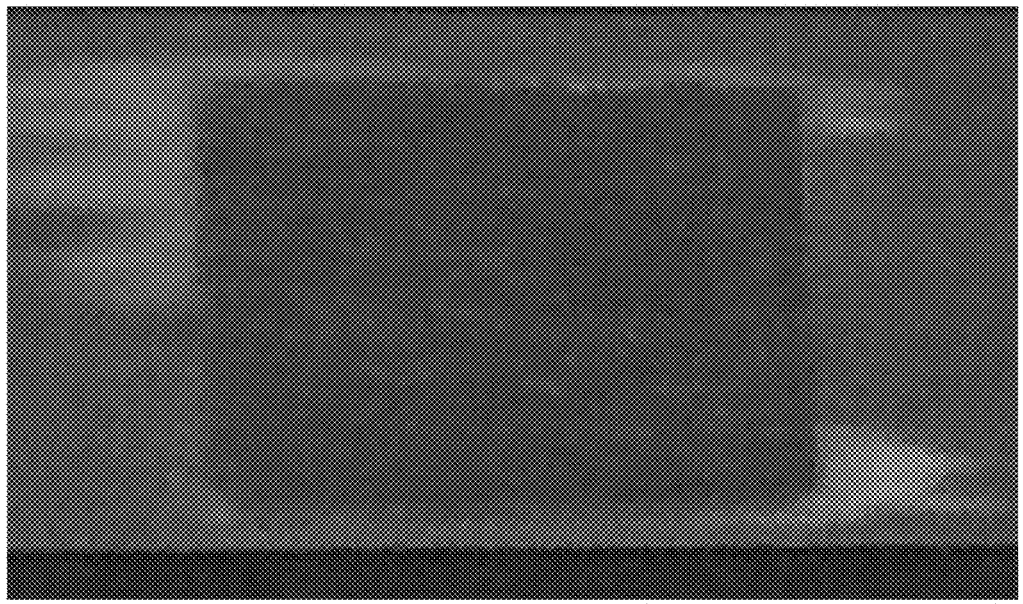
FIG. 2 illustrates a strip test according to the present invention that has been contacted with a sample of a substance that may cause an adverse effect to an individual. The substance is a sample of the anti-depressant. The test strip turns a dark color, and does not possess the bright yellow color of the positive test.

For testing, the strip test prepared above in Example 4 is placed under UV light, and contacted with the specimen of substance prepared above. The contacted test strip is then immediately observed under UV light in a dark room. In the presence of a predicted adverse reaction of the substance, the strip test will show the absence of fluorescence, or the fluorescence will decrease, or even completely disappear over a short period of time (about 90 seconds). If the substance is predicted to not cause an adverse reaction (that is, the absence of an adverse reaction), the strip test will remain fluorescent, at least for the duration of the test. According to an embodiment, strip tests are 90-second tests. The observation of the strip tests should take place within 90 seconds. The window of observation is between 60 seconds and 180 seconds. See FIGS. 1 and 2 for comparisons of positive and negative test strips. According to an embodiment, the degree by which fluorescence disappears after initial exposure to the substance may be used to quantify the relative adverseness of the substance. For example, a slow disappearance of fluorescence represents a less adverse substance than a substance for which the fluorescence disappears rapidly over the course of the testing procedure.

The strip test is not to serve as a diagnosis test, but as a screening to determine the susceptibility of people to chemicals.

EXAMPLE 6

Screening Composition 2

The baseline formulation "A" is prepared by mixing the listed ingredients according to the method described below in example 8. The quantities and concentrations are shown as the preferred quantity/concentration, and over a range of quantities and concentrations.

TABLE 5

Baseline for Positive Charge Strip Test "A" (for 100 ml of solution)

| Ingredient | Quantity | Concentration |
|---|---|---|
| Gram's iodine solution | 96.30 ml | Iodine 0.33% (w/v) and potassium iodide 0.66% (w/v) in water |
| Antimony oxide | 0.012 g | 0.012% w/v |
| | 0.010 g-0.014 g | 0.010% w/v-0.014% w/v |
| Magnesium oxide | 0.008 g | 0.008% w/v |
| | 0.007 g-0.009 g | 0.007% w/v-0.009% w/v |
| Potassium carbonate | 0.01 g | 0.01% w/v |
| | 0.009 g-0.012 g | 0.009% w/v-0.012% w/v |
| Magnesium hydroxide carbonate | 0.0115 g | 0.0115% w/v |
| | 0.0098 g-0.0132 g | 0.0098% w/v-0.0132% w/v |
| Lead (IV) oxide | 0.011 g | 0.011% w/v |
| | 0.009 g-0.013 g | 0.009% w/v-0.013% w/v |
| Boric anhydride | 0.008 g | 0.008% w/v |
| | 0.007 g-0.009 g | 0.007% w/v-0.009% w/v |
| Nickel (II) oxide | 0.0098 g | 0.0098% w/v |
| | 0.0083 g-0.0113 g | 0.0083% w/v-0.0113% w/v |
| Gallium (III) oxide | 0.006 g | 0.006% w/v |
| | 0.005 g-0.007 g | 0.005% w/v-0.007% w/v |
| Scandium (III) oxide | 0.008 g | 0.008% w/v |
| | 0.007 g-0.009 g | 0.007% w/v-0.009% w/v |
| Copper (II) oxide-black | 0.0089 g | 0.0089% w/v |
| | 0.0076 g-0.0102 g | 0.0076% w/v-0.0102% w/v |
| Iron (III) oxide | 0.0105 g | 0.0105% w/v |
| | 0.0089 g-0.0121 g | 0.0089% w/v-0.0121% w/v |

TABLE 5-continued

Baseline for Positive Charge Strip Test "A" (for 100 ml of solution)

| Ingredient | Quantity | Concentration |
|---|---|---|
| Lanthanum (III) oxide | 0.00912 g | 0.00912% w/v |
|  | 0.00776 g-0.01049 g | 0.00776%w/v-0.01049% w/v |
| Chromium (III) oxide | 0.01 g | 0.01% w/v |
|  | 0.009 g-0.012 g | 0.009% w/v-0.012% w/v |
| Tin powder | 0.00798 g | 0.00798% w/v |
|  | 0.00678 g-0.00918 g | 0.00678% w/v-0.00918% w/v |
| Calcium carbonate | 0.01 g | 0.01% w/v |
|  | 0.009 g-0.012 g | 0.009% w/v-0.012% w/v |
| Lithium carbonate | 0.0112 g | 0.0112 % w/v |
|  | 0.0095 g-0.0129 g | 0.0095% w/v-0.0129% w/v |
| Eosin Y disodium salt | 0.0998 g | 0.0998% w/v |
|  | 0.0848 g-0.1148 g | 0.0848% w/v-0.1148% w/v |
| Fluorescein sodium salt | 0.105 g | 0.105% w/v |
|  | 0.089 g-0.121 g | 0.089% w/v-0.121% w/v |
| Calcein disodium salt | 0.00934 g | 0.00934% w/v |
|  | 0.00793 g-0.01074 g | 0.00793% w/v-0.01074% w/v |

TABLE 6

Extended for Positive Charge Strip Test "B" (for 100 ml)

| Ingredient | Quantity | Concentration |
|---|---|---|
| Titanium dioxide slurry | 94.30 ml | 60-70% w/v |
| Sulfur powder | 0.011 g | 0.011% w/v |
|  | 0.009 g-0.013 g | 0.009% w/v-0.013% w/v |
| Aluminum oxide | 0.011 g | 0.011% w/v |
|  | 0.009 g-0.013 g | 0.009% w/v-0.013% w/v |
| Vanadium (V) oxide | 0.00995 g | 0.00995% w/v |
|  | 0.00846 g-0.01144 g | 0.00846% w/v-0.01144% w/v |
| Tungsten (VI) oxide | 0.00985 g | 0.00985% w/v |
|  | 0.00837 g-0.01133 g | 0.00837% w/v-0.01133% w/v |
| Molybdenum (VI) oxide | 0.00892 g | 0.00892% w/v |
|  | 0.00758 g-0.01026 g | 0.00758% w/v-0.01026% w/v |
| Zirconium (IV) oxide | 0.00921 g | 0.00921% w/v |
|  | 0.00783 g-0.01059 g | 0.00783% w/v-0.01059%w/v |
| Neodymium oxide | 0.0112 g | 0.0112% w/v |
|  | 0.0095 g-0.0129 g | 0.0095% w/v-0.0129% w/v |
| Fluorescein dye content 95% (free acid) | 0.0921 g | 0.0921% w/v |
|  | 0.0783 g-0.1059 g | 0.0783% w/v-0.1059% w/v |
| Fluorescein Reag., Ph. Eur., free acid | 0.0999 g | 0.0999% w/v |
|  | 0.0849 g-0.1149 g | 0.0849% w/v-0.1149% w/v |
| Erythrosin yellowish blend | 0.0768 g | 0.0768% w/v |
|  | 0.0653 g-0.0883 g | 0.0653% w/v-0.0883% w/v |

EXAMPLE 7

Preparation of Test Strip Solid Phase Layer

TABLE 7

Ethanol and silica solution

| Ingredient | Quantity | Concentration |
|---|---|---|
| Ethanol | 250 ml | 100% v/v |
| Silica gel | 1.1 g | 1.1% w/v |
|  | 0.95 g-1.25 g | 0.95% w/v-1.25% w/v |

The ethanol and silica gel solution described above is left to rest at room temperature, and a Whatman Qualitative Filter Paper Grade 3 (e.g. CAT No. 1003-110 or No. 1003-090) is allowed to soak for at least four hours. When the soaking time is complete, the treated filter paper is removed and left to dry. After the filter is dried, the excess silica gel is brushed or blown off the filter paper.

After complete drying of the filter paper or strips cut therefrom may be used for screening purposes.

EXAMPLE 8

Preparation of the Screening Formulation

The chemicals of Table 5 are mixed together in a 250 ml beaker or equivalent container in the listed sequential order disclosed above. After each chemical is added, the mixture is stirred such that each new chemical added to the solution is immediately stirred and mixed with the other as it is added. After the chemicals of Table 5 have been mixed in sequential order, helium gas is bubbled through the solution by barbotage for a period of 20 to 30 seconds. After the helium gas has been added, the mixture is stirred and is then placed under plant light (blue light, e.g. ≈425-450 nm wavelength, 75 W indoor plant light bulb or equivalent) to facilitate the homogenous mixing of the chemical mixtures and reaction together. This process involving the plant light takes approximately 10 to 15 minutes, after which the solution is removed from the plant light.

Similarly, the chemicals of Table 6 are mixed together in a 250 ml beaker or equivalent container in the listed sequential order disclosed above. After each chemical is added, the mixture is stirred such that each new chemical added to the solution is immediately stirred and mixed with the other as it is added. After the chemicals of Table 6 have all been added and mixed in sequential order, nitrogen gas is bubbled through the solution by barbotage for a period of 20 to 30 seconds. After the nitrogen gas has been added, the mixture is stirred and is then placed under plant light (blue light, e.g. ≈425-450 nm wavelength, 75 W indoor plant light bulb or equivalent) to facilitate the homogenous mixing of the chemical mixtures and reaction together. This process involving the plant light takes approximately 10 to 15 minutes, after which the solution is removed from the plant light.

When the chemicals of Table 5 and Table 6 have been prepared, the Table 5 chemical solution is poured into the Table 6 solution and then stirred until homogenous (about 30 seconds). It is to be stored in a dark place for up to eight hours before painting. After the eight hours is complete, the mixture is then ready to be used for application to the filter solid support.

EXAMPLE 9

Preparation of Test Strips

The pre-treated Whatman filter paper prepared above is coated with the liquid screening formulation. Each strip test is coated with three layers of the liquid formulation, which are applied consecutively after the previous layer has been added.

Once the application of the three layers has been completed, the painted filter paper is placed under the same plant light for one hour. After one hour, the painted filter paper is transferred to a dehydrator for a period of 4 to 8 hours at a temperature of 62.7° C., until it is thoroughly dry.

EXAMPLE 10

Screening Test Procedure

Prior to testing, the specimen of substance to be tested is placed directly into a solvent. Preferably, the solvent is a solvent such as distilled or filtered water. If the specimen is in tablet form, it should be crushed into a powder and then added to the solvent. If the specimen is in another form, it is preferably disaggregated into small pieces. The powder or pieces are then left to sit in the solvent until mixed in and/or dissolved for a period ranging from a few seconds to minutes, hours or even days before it may be tested with the composition and/or strip test of the present invention. Preferably, the contact with the solvent is at least eight hours. A liquid or gel form can be put directly into the solvent. Any capsule contents can be emptied into the solvent without the encapsulation material. However, the actual capsule material by itself can also be tested.

For testing, the strip test prepared above is placed under UV light in a room with reduced lighting to allow the reaction to be observed, and is contacted with the specimen of substance prepared above. The contact test strip is then allowed to react for a period of 3 to 5 minutes, depending on the type of test, and then immediately observed. In the presence of a predicted adverse reaction of the substance, the strip test will show the absence of fluorescence or the fluorescence will decrease, or even completely disappear over the short period of time (about 3 to 5 minutes). If the substance is predicted to not cause an adverse reaction (i.e. the absence of an adverse reaction), the strip test will remain fluorescent at least for the duration of the test. Strip tests, for the most part, are three-minute tests. For most tests, the observation of the strip tests should take place within three minutes and the window of observation is between 60 to 180 seconds.

Figure 3:
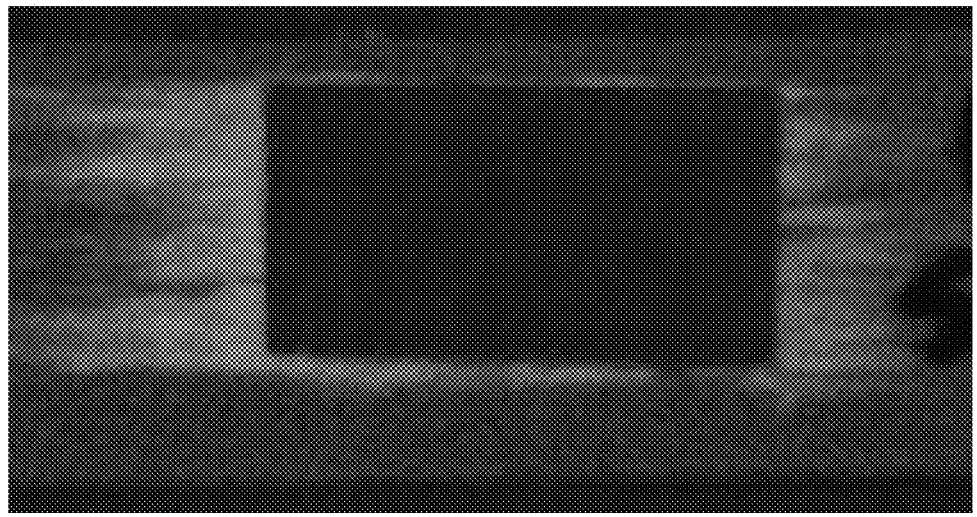
FIG. 3 illustrates a strip test according to the present invention that has been contacted with a sample of a substance that may cause an adverse effect to an individual. The substance is a sample of the anti-depressant Dextroamphetamine XR 5 mg. The test strip turns a dark color, and does not possess the bright yellow color of the positive test.
Figure 4:
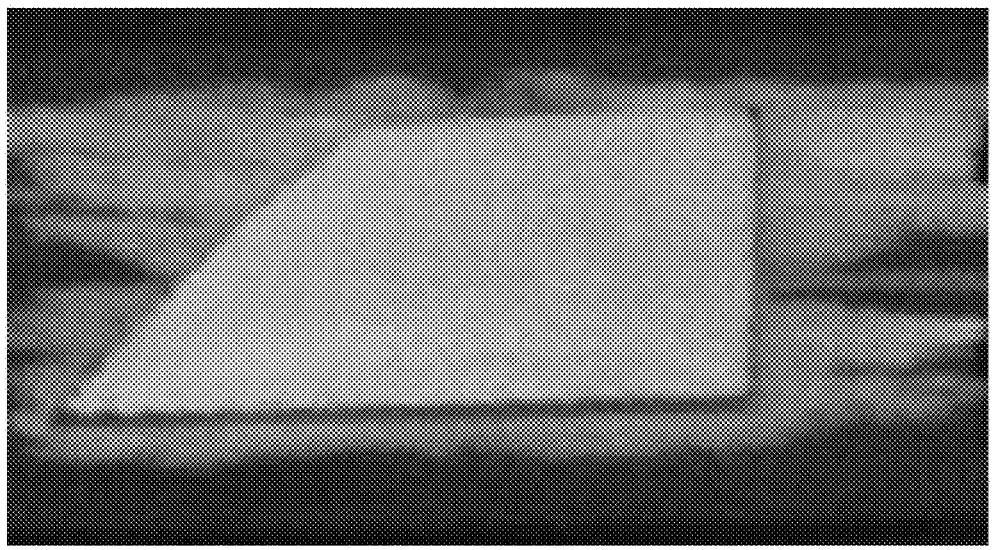
FIG. 4 illustrates a strip test according to the present invention that has been contacted with a sample of a substance that does not cause an adverse effect to an individual. The substance is a sample of the blood pressure medication candesartan 8 mg. The test strip glows a bright yellow color.
Figure 5:
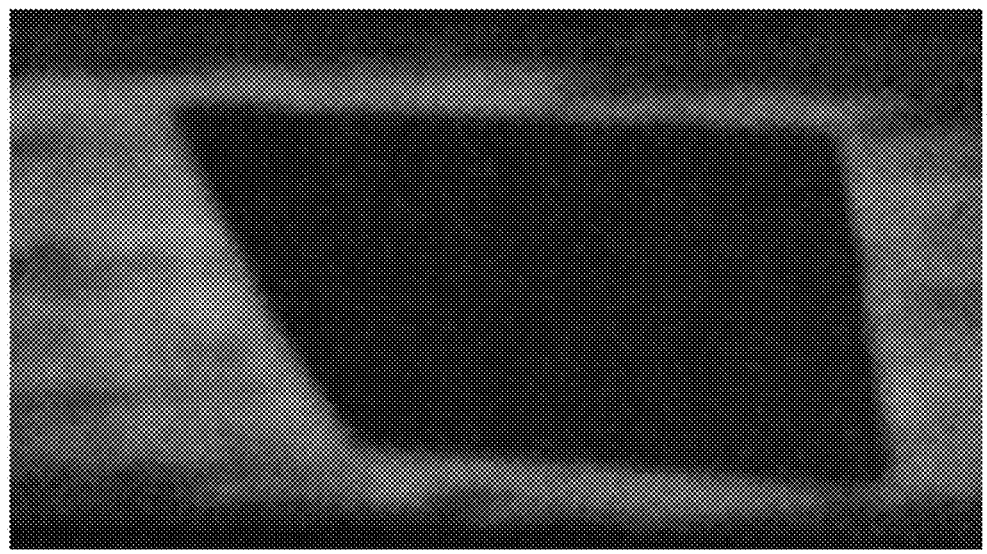
FIG. 5 illustrates a strip test according to the present invention that has been contacted with a sample of a substance that may cause an adverse effect to an individual.

See FIGS. 3 and 4 for comparisons of adverse and non-adverse reaction results. The degree by which fluorescence disappears after initial exposure to the substance may be used to quantify the relative adverseness of the substance. For example, a slow disappearance of fluorescence represents a less adverse substance than a substance for which the fluorescence disappears rapidly over the course of the testing procedure.

The strip test is not to serve as a diagnostic test, but as a screening to determine the susceptibility of people to chemicals.

EXAMPLE 11

Screening Composition 3

TABLE 8

Baseline for Positive Charge Strip Test "A" (for 100 ml of solution)

| Ingredient | Quantity | Concentration |
|---|---|---|
| Gram's iodine solution | 93.05 ml | Iodine 0.33% (w/v) and potassium iodide 0.66% (w/v) in water |
| Molybdenum (VI) oxide | 0.0446 g<br>0.0379 g-0.0513 g | 0.0446% w/v<br>0.0379% w/v-0.0513% w/v |
| Bismuth oxide | 0.03 g<br>0.026 g-0.034 g | 0.03% w/v<br>0.026% w/v-0.034% w/v |
| Magnesium oxide | 0.06 g<br>0.051 g-0.069 g | 0.06% w/v<br>0.051% w/v-0.069% w/v |
| Magnesium hydroxide carbonate | 0.058 g<br>0.049 g-0.067 g | 0.058% w/v<br>0.049% w/v-0.067% w/v |
| Gallium (III) oxide | 0.006 g<br>0.005 g-0.007 g | 0.006% w/v<br>0.005% w/v-0.007% w/v |
| Lead (II) oxide | 0.062 g<br>0.053 g-0.071 g | 0.062% w/v<br>0.053% w/v-0.071% w/v |

TABLE 8-continued

Baseline for Positive Charge Strip Test "A" (for 100 ml of solution)

| Ingredient | Quantity | Concentration |
|---|---|---|
| Copper (I) oxide | 0.071 g<br>0.06 g-0.082 g | 0.071% w/v<br>0.06% w/v-0.082% w/v |
| Calcium fluoride | 0.025 g<br>0.021 g-0.029 g | 0.025% w/v<br>0.021% w/v-0.029% w/v |
| Boric anhydride | 0.02 g<br>0.017 g-0.023 g | 0.02% w/v<br>0.017% w/v-0.023% w/v |
| Strontium titanate | 0.0244 g<br>0.0207 g-0.0281 g | 0.0244% w/v<br>0.0207% w/v-0.0281% w/v |
| Bismuth carbonate oxide | 0.06 g<br>0.051 g-0.069 | 0.06% w/v<br>0.051% w/v-0.069% w/v |
| Vanadium (V) oxide | 0.0498 g<br>0.0423 g-0.0573 g | 0.0498% w/v<br>0.0423% w/v-0.0573% w/v |
| Bismuth chloride oxide | 0.02 g<br>0.017 g-0.023 g | 0.02% w/v<br>0.017% w/v-0.023% w/v |
| Fluorescein disodium salt | 0.105 g<br>0.089 g-0.121 g | 0.105% w/v<br>0.089% w/v-0.121% w/v |
| Fluorescein Reag. Ph. Eur., free acid | 0.05 g<br>0.043 g-0.058 g | 0.05% w/v<br>0.043% w/v-0.058% w/v |
| Calcein disodium salt | 0.0093 g<br>0.0079 g-0.0107 g | 0.0093% w/v<br>0.0079% w/v-0.0107% w/v |

TABLE 9

Extended for Positive Charge Strip Test "B" (for 100 ml)

| Ingredient | Quantity | Concentration |
|---|---|---|
| Titanium dioxide slurry | 93.25 ml | 60-70% w/v |
| Nickel (II) oxide | 0.098 g<br>0.083 g-0.113 g | 0.098% w/v<br>0.083% w/v-0.113% w/v |
| Sulfur powder | 0.11 g<br>0.09 g-0.13 g | 0.11% w/v<br>0.09% w/v-0.13% w/v |
| Aluminum oxide | 0.11 g<br>0.09 g-0.13 g | 0.11% w/v<br>0.09% w/v-0.13% w/v |
| Zirconium (IV) oxide | 0.069 g<br>0.059 g-0.079 g | 0.069% w/v<br>0.059% w/v-0.079% w/v |
| Neodymium oxide | 0.056 g<br>0.048 g-0.064 g | 0.056% w/v<br>0.048% w/v-0.064% w/v |
| Fluorescein dye content 95% (free acid) | 0.1382 g<br>0.1175 g-0.1589 g | 0.1382% w/v<br>0.1175% w/v-0.1589% w/v |
| Azure Ponceau Stain | 1.00 ml | 0.001% w/v<br>0.0005% w/v-0.0015% w/v |

Explanation of Activator 1

The primary purpose of Activator 1 is believed to be to detect factors in the urine of the subject to indicate that the subject has experienced an adverse reaction to a food, drug, contaminant, pesticide or any other deleterious substance that can cause an adverse reaction to any human being or animal. We will assign the description of this first protein crystal as being Protein 1 for the purpose of this patent. Further, Protein 1 is a master protein crystal which is released when a human or animal body has been exposed to a food contaminant and/or pesticide. This protein is simply saying that the body is reacting in a negative way. The screening of this Protein 1 crystal will indicate to the subject that an investigation is warranted to understand the source of the food contaminant/pesticide that is causing the adverse reaction.

Explanation of Activator 2

The primary purpose of Activator 2 is to interact with a protein crystals expressed in the urine, allowing these crystals to unfold so that it can be tested. In addition, Activator 2 will allow other imaging/scientific equipment to be used to study the protein crystals under the correct scientific conditions much more effectively. The presence of this protein indicates that the subject has experienced an adverse reaction to a food, drug, contaminant, pesticide or any other substance, not limited to herein identified, that can cause an adverse reaction to any human being or animal. We will assign the description of this first protein crystal as being Protein 2 for the purpose of this patent. In addition to one experiencing an adverse reaction to a food contaminant/pesticide, Protein 2, when present in the urine, is an indicator that there is a chronic physical disease in the body as a result of being exposed to food contaminant/pesticide. The screening of this Protein 2 crystal will indicate to the subject that an investigation is warranted to understand the source of the food contaminant/pesticide that is causing the chronic disease. And furthermore, the screening will serve as a platform to understand what type of treatment is required after a full and complete diagnosis has been done on the subject.

Not all tests require an activator to stimulate the protein crystals that may exist in the human or animal urine.

TABLE 10

Activator 1

| Ingredient | Quantity | Concentration |
|---|---|---|
| Gram's iodine solution | 99.30 ml | Iodine 0.33% (w/v) and potassium iodide 0.66% (w/v) in water |
| Bismuth carbonate oxide | 0.022 g<br>0.0187 g-0.0253 g | 0.022% w/v<br>0.0187% w/v-0.0253%w/v |
| Magnesium hydroxide carbonate | 0.0115 g<br>0.0098 g-0.0132 g | 0.0115% w/v<br>0.0098% w/v-0.0132%w/v |
| Nickel (II) carbonate | 0.017 g<br>0.014 g-0.020 g | 0.017% w/v<br>0.014% w/v-0.020% w/v |
| Tellurium oxide | 0.0091 g<br>0.0077 g-0.0105 g | 0.0091% w/v<br>0.0077% w/v-0.0105% w/v |
| Cesium bromide | 0.00812 g<br>0.00690 g-0.00934 g | 0.00812% w/v<br>0.00690% w/v-0.00934% w/v |

TABLE 11

Activator 2

| Ingredient | Quantity | Concentration |
|---|---|---|
| Gram's iodine solution | 98.00 ml | Iodine 0.33% (w/v) and potassium iodide 0.66% (w/v) in water |
| Bismuth carbonate oxide | 0.0275 g<br>0.0234 g-0.0316 g | 0.0275% w/v<br>0.0234% w/v-0.0316% w/v |
| Sodium bicarbonate | 0.0445 g<br>0.0378 g-0.0512 g | 0.0445% w/v<br>0.0378% w/v-0.0512% w/v |
| Copper (I) oxide | 0.0475 g<br>0.0404 g-0.0546 g | 0.0475% w/v<br>0.0404% w/v-0.0546% w/v |
| Calcium fluoride | 0.05 g<br>0.04 g-0.06 g | 0.05% w/v<br>0.04% w/v-0.06% w/v |
| Magnesium oxide | 0.02 g<br>0.017 g-0.023 g | 0.02% w/v<br>0.017% w/v-0.023% w/v |

EXAMPLE 12

Preparation of Test Strip Solid Phase Layer

TABLE 11

Preparation of Test Strip Solid Phase Layer

| Ingredient | Quantity | Concentration |
|---|---|---|
| Ethanol | 250 ml | 100% v/v |
| Silica gel | 1.1 g<br>0.95 g-1.25 g | 1.1% w/v<br>0.95% w/v-1.25% w/v |

The ethanol and silica gel solution described above is left to rest at room temperature, and a Whatman Qualitative Filter Paper Grade 3 (e.g. CAT No. 1003-110 or No. 1003-090) is allowed to soak for at least four hours. When the soaking time is complete, the treated filter paper is removed and left to dry. After the filter is dried, the excess silica gel is brushed or blown off the filter paper.

After complete drying of the filter paper or strips cut therefrom, it may be used for screening purposes.

EXAMPLE 13

Preparation of the Screening Formulation

The chemicals of Table 8 are mixed together in a 250 ml beaker or equivalent container in the listed sequential order disclosed above. After each chemical is added, the mixture is stirred such that each new chemical added to the solution is immediately stirred and mixed with the other as it is added. After the chemicals of Table 8 have been mixed in sequential order, the mixture is stirred and is then placed under plant light (blue light, e.g. ≈425-450 nm wavelength, 75 W indoor plant light bulb or equivalent) to facilitate the homogenous mixing of the chemical mixtures and reaction together. This process involving the plant light takes approximately 30 minutes, after which the solution is removed from the plant light.

Similarly, the chemicals of Table 9 are mixed together in a 250 ml beaker or equivalent container in the listed sequential order disclosed above. After each chemical is added, the mixture is stirred such that each new chemical added to the solution is immediately stirred and mixed with the other as it is added. After the chemicals of Table 9 have all been added and mixed in sequential order, the mixture is stirred and is then placed under plant light (blue light, e.g. ≈425-450 nm wavelength, 75 W indoor plant light bulb or equivalent) to facilitate the homogenous mixing of the chemical mixtures and reaction together. This process involving the plant light takes approximately 30 minutes, after which the solution is removed from the plant light.

When the chemicals of Table 8 and Table 9 have been prepared, the Table 8 chemical solution is poured into the Table 9 solution and then stirred until homogenous (about 30 seconds). It is to be stored in a dark place for up to eight hours before painting. After the eight hours is complete, the mixture is then ready to be used for application to the filter solid support.

EXAMPLE 14

Preparation of Test Strips

The pre-treated Whatman filter paper prepared above is coated with the liquid screening formulation. Each strip test is coated with three layers of the liquid formulation, which are applied consecutively after the previous layer has been added.

Once the application of the three layers has been completed, the painted filter paper is placed under the same plant light for one hour. After one hour, the painted filter paper is transferred to a dehydrator for a period of 4 to 8 hours at a temperature of 62.7° C., until it is thoroughly dry.

EXAMPLE 15

Preparation of the Activators

The mixing procedure for each activator is the same; only the ingredients differ. The following procedure applies for the mixing of Activator 1 and Activator 2.

The chemicals of the activator are mixed together in a 250 ml beaker or equivalent container in the listed sequential order disclosed above. After each chemical is added, the mixture is stirred such that each new chemical added to the solution is immediately stirred and mixed with the other as it is added. After the chemicals of the activator have been mixed in sequential order, the mixture is stirred and is then placed under plant light (blue light, e.g. ≈425-450 nm wavelength, 75 W indoor plant light bulb or equivalent) to facilitate the homogenous mixing of the chemical mixtures and reaction together. This process involving the plant light takes approximately three hours, after which the solution is removed from the plant light. It is then placed in a sunlight-protected dark glass bottle with the lid tightly sealed. It should then be stored in a dark place, away from sunlight.

EXAMPLE 16

Screening Test Procedure

Once the urine has been provided, it needs to be cooled to a temperature of 18.3° C. This is the best temperature for testing in this case. When preparing for the test, the urine should be divided into two different groups. The first group is to add Activator 1 and observe the reaction. The second group is to add Activator 2 and observe the reaction.

To perform the Activator 1 test, take approximately 20 ml of urine and add 5 ml of the activator solution. Allow this to sit for 20 minutes under ultraviolet light. Once the 20 minutes has passed, place the strip test under ultraviolet light in a darkened room and apply approximately 1 ml of urine/Activator 1 solution onto the strip test. After the urine/Activator 1 solution has been applied to the strip test, one simply observes the reaction. If the fluorescein disappears, it is confirmation that factors likely are present in the urine. The same test can be repeated three times.

Activator 2 urine strip test follows under the same procedures as Activator 1.

The suggested time is between 3 to 5 minutes, preferably 3 minutes.

See FIGS. 5 to 8 for comparisons of presence and absence of the contaminant biomarkers (protein crystals) reaction results. The degree by which fluorescence disappears after initial exposure of urine/activator to the strip test may be used to quantify the relative presence of the factor in the urine. For example, a slow disappearance of fluorescence represents less presence of the pesticide biomarker than a urine/activator sample for which the fluorescence disappears rapidly over the course of the testing procedure.

The strip test is not to serve as a diagnostic test, but as a screening to confirm if someone is having an adverse reaction to any food or substance and to screen if the food or substance has triggered a chronic disease and/or chronic chemical imbalance that may lead to a chronic disease. The screening strip test is to serve as a tool for the scientific and medical communities to help better understand which foods and substances are potentially harmful to humans. By observing different subjects, what conclusions can be made as to the type of harm certain foods and substances may cause injury to humans or to animals.

EXAMPLE 17

Screening of Various Compounds

Now referring to FIG. 9, a panel of common pain relief medication—ASA, and ibuprofen were screened, in increasing amounts dissolved in 50 ml of filtered water, with the strip test of the present invention from Example 1. Increasing amounts of ASA appears to be adverse, while increasing amounts of ibuprofen is not.

Now referring to FIG. 10, the pain relief medication—ASA, ibuprofen and acetaminophen were screened in the presence of alcohol (Ethanol)—50 ml water and 50 ml of 40% vol/vol ethanol. Alcohol alone appears to be adverse, while the presence of ASA, ibuprofen and acetaminophen diminishes adverseness to varying degrees.

Now referring to FIG. 11, various sweetening agents or table salts were dissolved in 75 ml of filtered water and exposed to UV lamp for 3 minutes or 5 minutes. Sugar cane sugar appears to not be adverse, while icing sugar is dimmer. Sucralose appears to be initially not adverse, but a 5 minute exposure shows depleted fluorescence, indicative of a mild adverse effect. Sodium chloride (iodized) appears to not be adverse, while Himalayan pink salt appears to be initially not adverse, but a 5 minute exposure shows depleted fluorescence, indicative of a mild adverse effect.

Now referring to FIG. 12, urine from two distinct individuals to screen for any potential active chronic adverse activity that may need to be further investigated to sort out the cause. The test was done using two different urine samples, 3 minutes and 5 minutes time elapsed. The first individual appears to not be the subject of any adverse effect, while the second does.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:
1. A screening composition comprising:
  a marker compound, chosen from at least one of iodine, and fluorescein; eosin Y, erythrosine, ponceau S, calcein,
  a catalyst, chosen from at least one boron trioxide ($B_2O_3$), potassium (K), Gallium (III) oxide ($Ga_2O_3$), Nickel (II) oxide (NiO), Vanadium (V) oxide ($V_2O_5$), magnesium oxide (MgO), a bismuth oxide chosen from bismuth subcarbonate [$Bi_2O_2(CO_3)$], bismuth chloride oxide (BiClO), and bismuth oxide ($Bi_2O_3$), cesium bromide (CsBr), lanthanum (III) oxide ($La_2O_3$), molybdenum (VI) oxide ($MoO_3$), neodymium oxide ($Nd_2O_3$), Nickel (II) carbonate anhydrous ($NiCO_3$); and
  a pigment, chosen from at least one of scandium (III) oxide ($Sc_2O_3$), Lead (IV) oxide ($PbO_2$), Sulfur (S) powder, and Tungsten (VI) oxide ($WO_3$), chromium

(III) oxide ($Cr_2O_3$), copper (II) oxide (CuO), copper (I) oxide ($Cu_2O$), iron (III) oxide ($Fe_2O_3$), lead (II) oxide (PbO).

2. The screening composition of claim 1, further comprising an additional ingredient comprising: calcium fluoride ($CaF_2$), Tin (Sn), tellurium (IV) oxide ($TeO_2$), Zirconium (IV) oxide ($ZrO_2$).

3. The screening composition of claim 1, further comprising a pH adjusting agent chosen from Acetic Acid, Adipic Acid, Ammonium Aluminum Sulphate, Ammonium Bicarbonate, Ammonium Carbonate, Ammonium Citrate, dibasic, Ammonium Citrate, monobasic, Ammonium Hydroxide, Ammonium Phosphate, dibasic, Ammonium Phosphate, monobasic, Calcium Acetate, Calcium Acid Pyrophosphate, Calcium Carbonate, Calcium Chloride, Calcium Citrate, Calcium Fumarate, Calcium Gluconate, Calcium Hydroxide, Calcium Lactate, Calcium Oxide, Calcium Phosphate, dibasic, Calcium Phosphate, monobasic, Calcium Phosphate, tribasic, Calcium Sulphate, Carbon Dioxide, Citric Acid, Cream of Tartar, Fumaric Acid, Gluconic Acid, Glucono-delta-lactone, Hydrochloric Acid, Lactic Acid, Magnesium Carbonate, Magnesium Citrate, Magnesium Fumarate, Magnesium Hydroxide, Magnesium Oxide, Magnesium Phosphate, Magnesium Sulphate, Malic Acid, Manganese Sulphate, Metatartaric Acid, Phosphoric Acid, Potassium Acid Tartrate, Potassium Aluminum Sulphate, Potassium Bicarbonate, Potassium Carbonate, Potassium Chloride, Potassium Citrate, Potassium Fumarate, Potassium Hydroxide, Potassium Lactate, Potassium Phosphate, dibasic, Potassium Sulphate, Potassium Tartrate, Sodium Acetate, Sodium Acid Pyrophosphate, Sodium Acid Tartrate, Sodium Aluminum Phosphate, Sodium Aluminum Sulphate, Sodium Bicarbonate, Sodium Bisulphate, Sodium Carbonate, Sodium Citrate, Sodium Fumarate, Sodium Gluconate, Sodium Hexametaphosphate, Sodium Hydroxide, Sodium Lactate, Sodium Phosphate, dibasic, Sodium Phosphate, monobasic, Sodium Phosphate, tribasic, Sodium Potassium Tartrate, Sodium Pyrophosphate, tetrabasic, Sodium Tripolyphosphate, Sulphuric Acid, Sulphurous Acid, Tartaric Acid, lithium carbonate, magnesium hydroxide carbonate.

4. The screening composition of claim 3, wherein said pH adjusting agent is chosen from potassium carbonate, magnesium carbonate, lithium carbonate, magnesium hydroxide carbonate.

5. The screening composition of claim 3, wherein said composition comprises:
   from about 0.44% to about 0.47% w/v iodine;
   from about 0.013% to about 0.017% antimony oxide;
   from about 0.025% to about 0.035% w/v magnesium oxide;
   from about 0.045% to about 0.05% w/v potassium carbonate;
   from about 0.04% to about 0.05% w/v magnesium carbonate;
   from about 0.045% to about 0.065% w/v lead (IV) oxide;
   from about 0.025% to about 0.065% w/v boric anhydride;
   from about 0.045% to about 0.055% w/v nickel (II) oxide;
   from about 0.013% to about 0.017% w/v gallium (III) oxide;
   from about 0.017% to about 0.023% w/v scandium (III) oxide;
   from about 0.045% to about 0.065% w/v sulfur powder;
   from about 0.045% to about 0.055% w/v vanadium (V) oxide;
   from about 0.05% to about 0.07% w/v tungsten (VI) oxide;
   from about 0.09% to about 0.12% w/v fluorescein disodium salt.

6. The screening composition of claim 3, wherein said composition comprises:
   from about 0.44% to about 0.47% w/v iodine;
   from about 0.005% to about 0.007% antimony oxide;
   from about 0.0035% to about 0.0045% w/v magnesium oxide;
   from about 0.0045% to about 0.006% w/v potassium carbonate;
   from about 0.005% to about 0.007% w/v magnesium hydroxide carbonate;
   from about 0.0045% to about 0.0065% w/v lead (IV) oxide;
   from about 0.0035% to about 0.0045% w/v boric anhydride;
   from about 0.004% to about 0.007% w/v nickel (II) oxide;
   from about 0.0025% to about 0.0035% w/v gallium (III) oxide;
   from about 0.0035% to about 0.0045% w/v scandium (III) oxide;
   from about 0.0038% to about 0.0051% w/v copper (II) oxide;
   from about 0.0045% to about 0.0061% w/v iron (III) oxide;
   from about 0.0039% to about 0.0052% w/v lanthanum (III) oxide;
   from about 0.0045% to about 0.006% w/v Chromium (III) oxide;
   from about 0.004% to about 0.005% w/v tin;
   from about 0.0045% to about 0.006% w/v calcium carbonate;
   from about 0.0048% to about 0.0065% w/v lithium carbonate;
   from about 0.0045% to about 0.0065% w/v sulfur powder;
   from about 0.043% to about 0.055% w/v vanadium (V) oxide;
   from about 0.0042% to about 0.0055% w/v tungsten (VI) oxide;
   from about 0.0038% to about 0.0051% w/v molybdenum (VI) oxide;
   from about 0.0039% to about 0.0053% w/v zirconium (IV) oxide;
   from about 0.0048% to about 0.0065% w/v neodymium oxide;
   from about 0.08% to about 0.11% w/v fluorescein;
   from about 0.042% to about 0.056% w/v eosin Y disodium salt;
   from about 0.045% to about 0.06% w/v fluorescein disodium salt;
   from about 0.004% to about 0.0053% w/v calcein disodium salt;
   from about 0.033% to about 0.044% w/v erythrosine yellowish blend.

7. The screening composition of claim 3, wherein said composition comprises:
   from about 0.44% to about 0.47% w/v iodine;
   from about 0.019% to about 0.025% molybdenum oxide;
   from about 0.013% to about 0.017% bismuth oxide;
   from about 0.026% to about 0.035% w/v magnesium oxide;
   from about 0.025% to about 0.034% w/v magnesium hydroxide carbonate;
   from about 0.027% to about 0.036% w/v lead (II) oxide;
   from about 0.009% to about 0.012% w/v boric anhydride;
   from about 0.04% to about 0.06% w/v nickel (II) oxide;

from about 0.03% to about 0.041% w/v copper (I) oxide;
from about 0.01% to about 0.015% w/v calcium fluoride;
from about 0.01% to about 0.014% w/v strontium titanate;
from about 0.026% to about 0.035% w/v bismuth carbonate oxide;
from about 0.045% to about 0.065% w/v sulfur powder;
from about 0.021% to about 0.029% w/v vanadium (V) oxide;
from about 0.009% to about 0.011% w/v bismuth chloride oxide;
from about 0.03% to about 0.04% w/v zirconium (IV) oxide;
from about 0.025% to about 0.032% w/v neodymium oxide;
from about 0.08% to about 0.11% w/v fluorescein;
from about 0.045% to about 0.06% w/v fluorescein disodium salt;
from about 0.004% to about 0.0054% w/v calcein disodium salt;
from about 0.00025% to about 0.0007% w/v ponceau S.

8. A screening strip comprising
an solid phase layer, comprising an adsorbent; and
a screening composition according to claim 1.

9. The screening strip of claim 8, wherein said adsorbent is at least one of silica gel ($SiO_2$), titanium dioxide ($TiO_2$), an aluminum oxide, strontium titanate ($SrTiO_3$), or a cellulose.

10. The screening strip of claim 9, wherein said titanium dioxide is from about 30% to 35% w/v of said solid phase layer.

11. The screening strip of claim 9, wherein said aluminum oxide ($Al_2O_3$) is from about 0.045% to 0.065% w/v, or from about 0.0045% to about 0.0065% w/v of said solid phase layer.

12. A method of screening for a sensitivity, intolerance or allergy to chemical substances comprising the steps of:
a) contacting a screening composition of claim 1, or a screening strip of claim 10 with a chemical substance;
b) measuring and comparing a fluorescence level from said screening composition or said screening strip contacted with said bodily fluid of said subject to a positive and/or negative control body fluid samples;
wherein a fluorescence level comparable to said negative control is indicative of an absence of sensitivity, intolerance or allergy;
wherein a fluorescence level intermediate to said negative control and said positive control is indicative of an intermediate level of sensitivity, intolerance or allergy; and
wherein absence of fluorescence is indicative of an presence of sensitivity, intolerance or allergy.

13. A method of screening for a sensitivity, intolerance or allergy to chemical substances in a subject comprising the steps of:
a) contacting a screening composition of claim 1, or a screening strip of claim 10 with a bodily fluid of said subject;
b) measuring and comparing a fluorescence level from said screening composition or said screening strip contacted with said bodily fluid of said subject to a positive and/or negative control body fluid samples;
wherein a fluorescence level comparable to said negative control is indicative of an absence of sensitivity, intolerance or allergy;
wherein a fluorescence level intermediate to said negative control and said positive control is indicative of an intermediate level of sensitivity, intolerance or allergy; and
wherein absence of fluorescence is indicative of an presence of sensitivity, intolerance or allergy.

14. The method of claim 13, further comprising the step of discontinuing use of said chemical substances, continuing use of said chemical substances, or increasing or decreasing the level of use of said chemical substance based on said method.

15. The method of claim 13, further comprising the step a") prior to performing said method:
a") obtaining a bodily fluid from said subject prior to use of said chemical substance.

16. The method of claim 13, further comprising contacting said screening composition or said screening strip contacted with said bodily fluid of said subject with an activator composition prior to step b).

17. The method of claim 16, wherein said activator composition comprises:
from about 0.44% to about 0.47% w/v iodine;
from about 0.009% to about 0.013% w/v bismuth carbonate oxide;
from about 0.0005% to about 0.0066% w/v magnesium hydroxide carbonate;
from about 0.007% to about 0.01% w/v nickel (II) carbonate;
from about 0.0039% to about 0.0053% w/v tellurium oxide; and
from about 0.0035% to about 0.005% w/v cesium bromide.

18. The method of claim 16, wherein said activator composition comprises:
from about 0.44% to about 0.47% w/v iodine;
from about 0.012% to about 0.016% w/v bismuth carbonate oxide;
from about 0.019% to about 0.026% w/v sodium bicarbonate;
from about 0.02% to about 0.027% w/v copper (I) oxide;
from about 0.02% to about 0.03% w/v calcium fluoride; and
from about 0.0009% to about 0.0012% w/v magnesium oxide.

19. The method of claim 15, further comprising the step a') prior to performing said method:
a') obtaining a bodily fluid from said subject after use of said chemical substance.

* * * * *